US012733890B2

(12) United States Patent
Ather et al.

(10) Patent No.: US 12,733,890 B2
(45) Date of Patent: Sep. 15, 2026

(54) ELECTRONICALLY STEERABLE X-RAY IMAGING SYSTEM FOR PRECISION BREAST CANCER DETECTION

(71) Applicants: Syed Hussain Ather, Zionsville, IN (US); Richard Gordon, Alonsa (CA)

(72) Inventors: Syed Hussain Ather, Zionsville, IN (US); Richard Gordon, Alonsa (CA)

( * ) Notice: Subject to any disclaimer, the term of this patent is extended or adjusted under 35 U.S.C. 154(b) by 0 days.

(21) Appl. No.: 19/364,778

(22) Filed: Oct. 21, 2025

(65) Prior Publication Data

US 2026/0041383 A1 Feb. 12, 2026

(51) Int. Cl.

| | |
|---|---|
| ***A61B 6/40*** | (2024.01) |
| ***A61B 6/00*** | (2024.01) |
| ***A61B 6/04*** | (2006.01) |
| ***A61B 6/50*** | (2024.01) |
| ***A61B 6/58*** | (2024.01) |

(52) U.S. Cl.

CPC ........... *A61B 6/405* (2013.01); *A61B 6/0414* (2013.01); *A61B 6/502* (2013.01); *A61B 6/5205* (2013.01); *A61B 6/5282* (2013.01); *A61B 6/583* (2013.01); *A61B 6/585* (2013.01)

(58) Field of Classification Search

None

See application file for complete search history.

(56) References Cited

U.S. PATENT DOCUMENTS

| | | | | |
|---|---|---|---|---|
| 2004/0162457 | A1* | 8/2004 | Maggiore | A61N 5/1079 600/1 |
| 2004/0208276 | A1* | 10/2004 | Kaufman | A61B 6/563 378/4 |
| 2005/0226375 | A1* | 10/2005 | Eberhard | A61B 6/584 378/62 |
| 2008/0002807 | A1* | 1/2008 | Debasish | G06T 11/006 378/7 |
| 2017/0007354 | A1* | 1/2017 | Krupnik | A61B 6/487 |
| 2021/0052330 | A1* | 2/2021 | Kiselyov | A61B 8/5269 |
| 2021/0369222 | A1* | 12/2021 | Fontaine | A61B 6/5205 |
| 2021/0383582 | A1* | 12/2021 | De Man | A61B 6/5264 |

* cited by examiner

*Primary Examiner* — Jonathan Cwern

(74) *Attorney, Agent, or Firm* — The Rapacke Law Group, P.A.; Andrew S. Rapacke; Kenneth F. Brooks

(57) ABSTRACT

An electronically steerable x-ray imaging system is disclosed that includes an x-ray beam generator, a Janus sphere array, a sensor array, and a computer system configured to reconstruct diagnostic images of biological tissue. The Janus sphere array enables electronic steering of the x-ray beam to control direction, intensity, and focus without mechanical movement. The sensor array collects x-ray data after beam transmission through an imaging target such as breast tissue, and the computer system executes a Multiplicative Algebraic Reconstruction Technique (MART) algorithm to reconstruct high-resolution images. The processor optimizes tumor visibility and reduces image noise by adaptively adjusting beam parameters in response to tissue density. The system provides real-time feedback and dynamic beam control for accurate tumor detection and improved imaging performance across medical and non-medical applications.

20 Claims, 8 Drawing Sheets

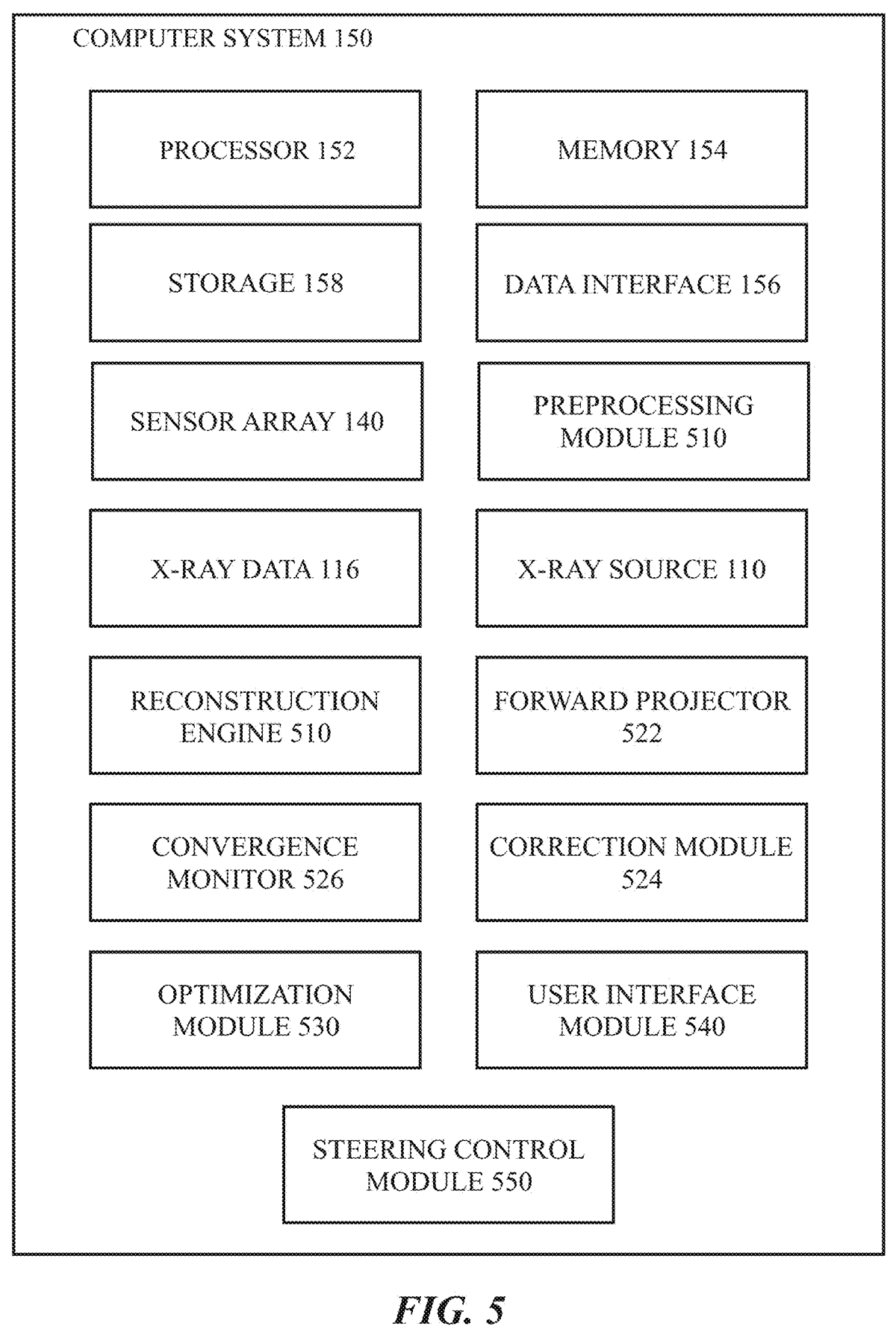

COMPUTER SYSTEM 150

PROCESSOR 152

MEMORY 154

STORAGE 158

DATA INTERFACE 156

SENSOR ARRAY 140

PREPROCESSING MODULE 510

X-RAY DATA 116

X-RAY SOURCE 110

RECONSTRUCTION ENGINE 510

FORWARD PROJECTOR 522

CONVERGENCE MONITOR 526

CORRECTION MODULE 524

OPTIMIZATION MODULE 530

USER INTERFACE MODULE 540

STEERING CONTROL MODULE 550

*FIG. 5*

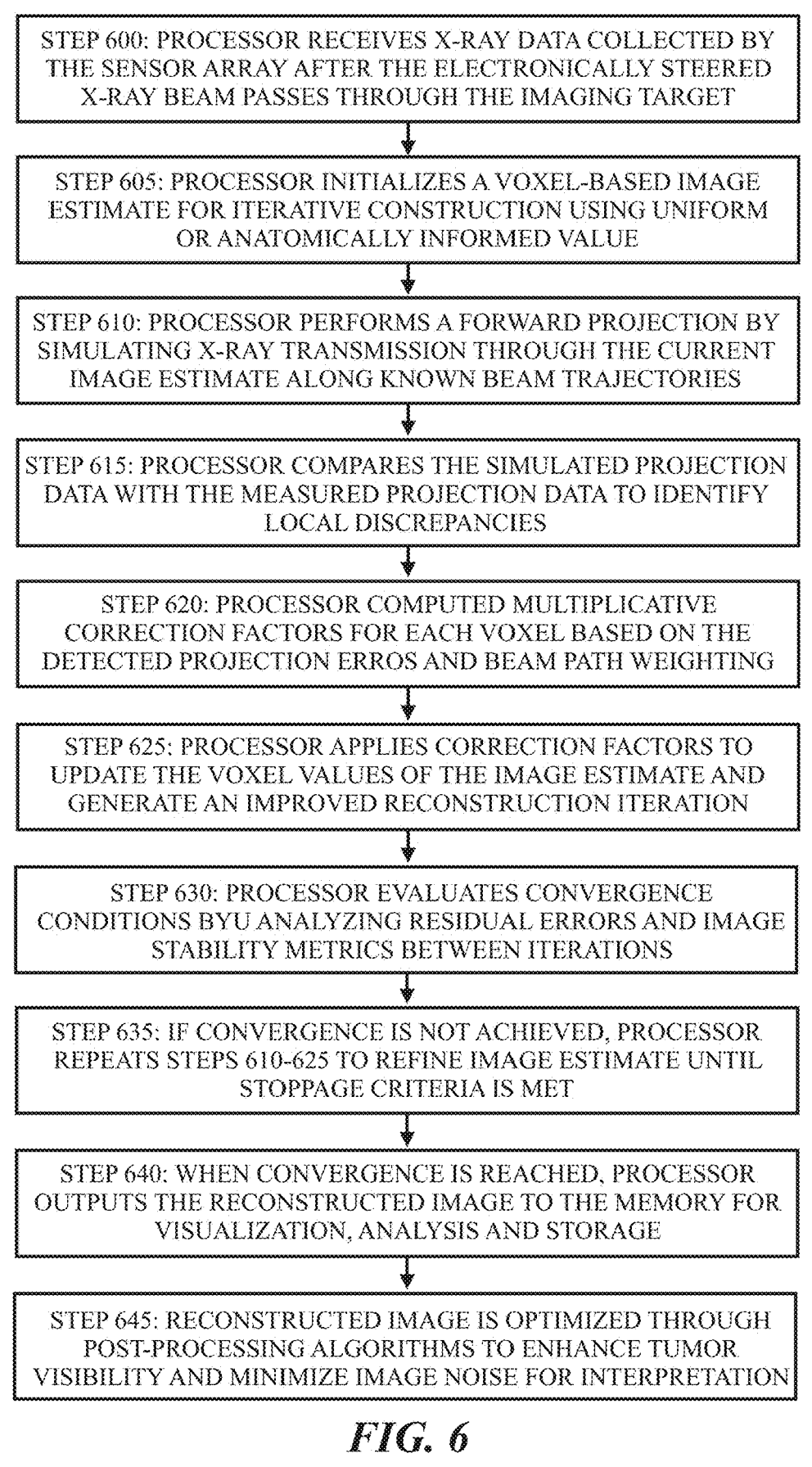

STEP 600: PROCESSOR RECEIVES X-RAY DATA COLLECTED BY THE SENSOR ARRAY AFTER THE ELECTRONICALLY STEERED X-RAY BEAM PASSES THROUGH THE IMAGING TARGET

STEP 605: PROCESSOR INITIALIZES A VOXEL-BASED IMAGE ESTIMATE FOR ITERATIVE CONSTRUCTION USING UNIFORM OR ANATOMICALLY INFORMED VALUE

STEP 610: PROCESSOR PERFORMS A FORWARD PROJECTION BY SIMULATING X-RAY TRANSMISSION THROUGH THE CURRENT IMAGE ESTIMATE ALONG KNOWN BEAM TRAJECTORIES

STEP 615: PROCESSOR COMPARES THE SIMULATED PROJECTION DATA WITH THE MEASURED PROJECTION DATA TO IDENTIFY LOCAL DISCREPANCIES

STEP 620: PROCESSOR COMPUTED MULTIPLICATIVE CORRECTION FACTORS FOR EACH VOXEL BASED ON THE DETECTED PROJECTION ERROS AND BEAM PATH WEIGHTING

STEP 625: PROCESSOR APPLIES CORRECTION FACTORS TO UPDATE THE VOXEL VALUES OF THE IMAGE ESTIMATE AND GENERATE AN IMPROVED RECONSTRUCTION ITERATION

STEP 630: PROCESSOR EVALUATES CONVERGENCE CONDITIONS BYU ANALYZING RESIDUAL ERRORS AND IMAGE STABILITY METRICS BETWEEN ITERATIONS

STEP 635: IF CONVERGENCE IS NOT ACHIEVED, PROCESSOR REPEATS STEPS 610-625 TO REFINE IMAGE ESTIMATE UNTIL STOPPAGE CRITERIA IS MET

STEP 640: WHEN CONVERGENCE IS REACHED, PROCESSOR OUTPUTS THE RECONSTRUCTED IMAGE TO THE MEMORY FOR VISUALIZATION, ANALYSIS AND STORAGE

STEP 645: RECONSTRUCTED IMAGE IS OPTIMIZED THROUGH POST-PROCESSING ALGORITHMS TO ENHANCE TUMOR VISIBILITY AND MINIMIZE IMAGE NOISE FOR INTERPRETATION

*FIG. 6*

ELECTRONICALLY STEERABLE X-RAY IMAGING SYSTEM FOR PRECISION BREAST CANCER DETECTION

TECHNICAL FIELD

The present invention relates to medical imaging systems and, more particularly, to electronically steerable x-ray systems for low-dose, high-precision breast cancer detection. It specifically addresses advancements in beam steering, scatter reduction, and image reconstruction for improved tumor visualization and localization at low x-ray dose.

BACKGROUND

Breast cancer detection has long relied on imaging technologies to identify tumors at an early and treatable stage. The earliest imaging techniques, such as conventional x-ray mammography, provided two-dimensional views of internal breast structures, allowing radiologists to detect abnormal masses or calcifications. Over time, breast imaging systems evolved to include sophisticated tools such as ultrasound and magnetic resonance imaging (MRI), each offering unique advantages in terms of tissue contrast, sensitivity, and anatomical coverage. These tools have become standard components of diagnostic protocols and have significantly contributed to early detection campaigns across the globe.

Despite these advancements, existing imaging modalities still face notable limitations, particularly when it comes to detecting small tumors in breast tissue. Mammography, although widely used, especially suffers from reduced sensitivity in patients with high breast density, leading to potential false negatives. Likewise, ultrasound is highly operator-dependent and lacks the resolution necessary for consistent, accurate diagnosis. MRI, while capable of detailed imaging, is costly, time-intensive, and not always accessible in routine clinical settings. These challenges create barriers to accurate early diagnosis and necessitate repeat or supplemental imaging that increases healthcare costs and delays treatment.

Another common issue across traditional imaging platforms is the exposure of the entire breast region to uniform radiation or signal energy. For example, x-ray based systems typically irradiate broad tissue areas regardless of whether specific regions are of clinical interest. This indiscriminate exposure contributes to increased radiation dosage without proportionate diagnostic value. Additionally, these systems often struggle to distinguish between benign and malignant structures, especially when tumors are smaller than 5 mm, further complicating the diagnostic process and contributing to unnecessary biopsies.

Conventional x-ray systems, particularly computed tomography (CT), have limited application in breast imaging due to the energy levels they employ. High-energy x-rays used in general-purpose CT scanners are not optimized for soft tissue like the breast, and result in excess scatter, low contrast resolution, and suboptimal tumor visibility. Moreover, current systems lack the ability to dynamically steer the x-ray beam, which restricts their precision and sensitivity in locating early-stage abnormalities.

SUMMARY OF THE INVENTION

This summary is provided to introduce a variety of concepts in a simplified form that is further disclosed in the detailed description of the embodiments. This summary is not intended for determining the scope of the claimed subject matter.

The present invention provides an electronically steerable x-ray imaging system designed to improve the precision and safety of breast cancer detection. The system combines low-dose x-ray generation, real-time beam steering, and adaptive image reconstruction to deliver high-resolution images of internal breast tissue structures. By integrating a steerable x-ray source, a deflection system utilizing Janus spheres, and a specialized image processing algorithm, the invention enhances tumor visibility while reducing unnecessary radiation exposure to normal tissues. Unlike conventional imaging systems that irradiate the entire breast uniformly, this system focuses beam energy only where needed. As a result, it achieves both improved diagnostic sensitivity and reduced scatter artifacts, particularly in dense breast tissue.

The electronically steerable x-ray source includes an x-ray beam generator that emits x-rays within an energy range between 30 and 50 keV, which is optimal for soft tissue imaging. These lower-energy emissions are sufficient to penetrate breast tissue while minimizing harmful exposure, making the system suitable for regular screenings. The x-ray source is mounted in a configuration that allows for dynamic steering of the emitted beam in real time, enabling precise direction and intensity adjustments during imaging. This ability to modulate the beam dynamically allows clinicians to focus on areas of interest without oversaturating surrounding tissue with radiation. As a result, the system can adapt its operation to patient-specific anatomy and diagnostic requirements.

Positioned downstream of the x-ray source is a sphere array, which enables further control over the path of the x-ray beam. In one embodiment, this array consists of Janus spheres, dual-material microspheres with different refractive indices, that deflect the x-ray beam at programable angles. These controlled deflections allow for beam convergence on targeted regions within the breast while minimizing scatter and improving overall image contrast. The combination of electronic steering and passive deflection using Janus spheres results in a hybrid targeting mechanism capable of sub-millimeter spatial accuracy. This architecture supports advanced applications such as microcalcification detection and interventional guidance.

An imaging target is situated within the system to receive the x-ray beam and may consist of either a patient's breast or a breast phantom used for testing. In clinical use, the breast is positioned in a fixed or semi-stabilized orientation to ensure beam alignment and repeatability across sessions. When used for simulation or calibration, the breast phantom replicates the heterogeneous densities and textures found in human tissue, allowing for robust validation of system performance. Regardless of the context, the imaging target is illuminated by a focused and steerable x-ray beam that has been dynamically shaped by upstream control elements. This facilitates accurate and consistent imaging of anatomical features across different patients and use cases.

A sensor array is positioned around or adjacent to the imaging target to detect x-ray data post-penetration through the breast. The array is configured to capture transmitted and scattered x-rays, generating a comprehensive data set for image reconstruction. Each sensor is calibrated to register low-energy x-rays with high sensitivity, enabling the system to operate effectively at reduced radiation levels. The collected data provides spatially resolved attenuation information necessary for identifying small tumors or tissue anomalies. These signals are then passed to a computing system responsible for reconstructing the final image.

The computer system includes a processor configured to receive the plurality of x-ray data from the sensor array and reconstruct a diagnostic image using a Multiplicative Algebraic Reconstruction Technique (MART) or other iterative computed tomography algorithm. This algorithm processes the sensor data iteratively, refining image quality over multiple cycles by focusing reconstruction efforts on informative beam paths. MART is especially effective in low-dose contexts, as it reduces noise and improves contrast without relying on high-intensity radiation. The result is a high-resolution image with enhanced visibility of tumors, microcalcifications, and other early indicators of malignancy. The processor is further configured to optimize tumor visibility and suppress background noise in the final image output.

One embodiment of the invention includes an adaptive computing system that automatically adjusts both steering parameters and imaging parameters based on real-time analysis of tissue density and structural features. This adaptive feedback mechanism allows the system to fine-tune beam focus and reconstruction parameters during an ongoing scan. For example, denser regions of tissue may require more focused beam delivery or algorithmic adjustments to improve contrast. By constantly recalibrating its imaging process, the system ensures consistent quality across patients with varying anatomical profiles. This capability represents a significant advancement over static imaging systems that cannot respond dynamically to patient variability.

Our embodiment of the invention focuses on the use of Janus spheres as the primary mechanism for beam steering. In this configuration, the Janus sphere array is designed to deflect x-ray beams with high angular precision, enabling the beam to reach specific tissue regions that may be difficult to image with conventional collimation. The Janus spheres are arranged in a fixed matrix or adjustable lattice and are fabricated from materials selected for their differential x-ray refractive properties. The resulting beam path can be finely controlled based on the angle and composition of the spheres, offering a compact and passive method for achieving beam modulation. This design is particularly advantageous in constrained or mobile imaging systems where mechanical steering may be impractical.

The invention also provides a system configuration capable of detecting tumors between approximately 2 and 4 millimeters in diameter, which exceeds the sensitivity of many current imaging technologies. Such tumors are generally premetastasis. This high level of spatial resolution is achieved through the synergy of targeted beam delivery, scatter minimization, and optimized image reconstruction. Small tumors or microcalcifications often represent the earliest signs of breast cancer and are crucial to identifying the disease at a stage when it is most treatable. By enabling detection at this scale, the system contributes to improved clinical outcomes and reduces the need for repeat imaging or exploratory biopsies. This capability also makes the system suitable for screening high-risk populations and for use in diagnostic follow-up protocols.

In another aspect, the invention discloses a method for detecting a tumor in human breast tissue using the electronically steerable x-ray imaging system. The method begins by positioning the patient such that the breast is in optical view of the steerable x-ray source and sensor array. Once aligned, the x-ray beam is electronically steered and focused on the imaging target using the Janus sphere array. The system dynamically adjusts the beam deflection angle in real time based on detected or expected tissue density gradients. This ensures optimal beam alignment across various tissue zones and compensates for anatomical irregularities during the scan.

Following beam exposure, a plurality of x-ray data is collected by the sensor array and transmitted to the computing system for processing. The data undergoes iterative reconstruction via the MART algorithm to generate a high-contrast image with minimized noise. The image is further refined through algorithmic optimization to enhance visibility of small tumors, calcifications, or abnormal structures. This method enables the detection of cancerous lesions at an earlier stage than traditional imaging systems, with improved safety and diagnostic reliability. The entire process is conducted with an emphasis on dose efficiency, making it suitable for routine clinical screening.

In certain embodiments of the method, the ability to control beam direction and intensity enables personalized imaging protocols tailored to individual patients. For example, the system can increase beam intensity selectively in denser regions or adjust reconstruction weighting factors based on known risk factors. Additionally, by limiting beam exposure to mostly clinically relevant zones, the method reduces cumulative radiation dose over time. This approach supports long-term patient monitoring and frequent imaging without significantly increasing radiation risks. The method may be further extended to imaging tasks outside the breast, including thyroid or lung cancer screening with similar accuracy and safety benefits.

The invention as described represents a transformative approach to medical imaging, addressing long-standing challenges in resolution, radiation exposure, and diagnostic sensitivity. By combining electronically steerable x-ray technology, Janus sphere beam modulation, and advanced reconstruction algorithms, the system delivers high-quality images with reduced patient risk. It is well-suited for both diagnostic and screening environments and may also be used to guide real-time interventional procedures such as biopsies. Moreover, its adaptable framework and modular components allow for future upgrades and integration with machine learning-based diagnostic tools. Collectively, the invention sets a new standard for precision imaging in breast cancer detection and beyond.

BRIEF DESCRIPTION OF THE DRAWINGS

A complete understanding of the present embodiments and the advantages and features thereof will be more readily understood by reference to the following detailed description when considered in conjunction with the accompanying drawings wherein:

FIG. 5 is a block diagram of the computer system and associated functional modules configured to perform image reconstruction and optimization, according to some embodiments; and FIG. 6 is a flowchart illustrating the steps of the MART algorithm performed by the processor for reconstructing an image from x-ray data, according to some embodiments.

DETAILED DESCRIPTION

Figure 1A:
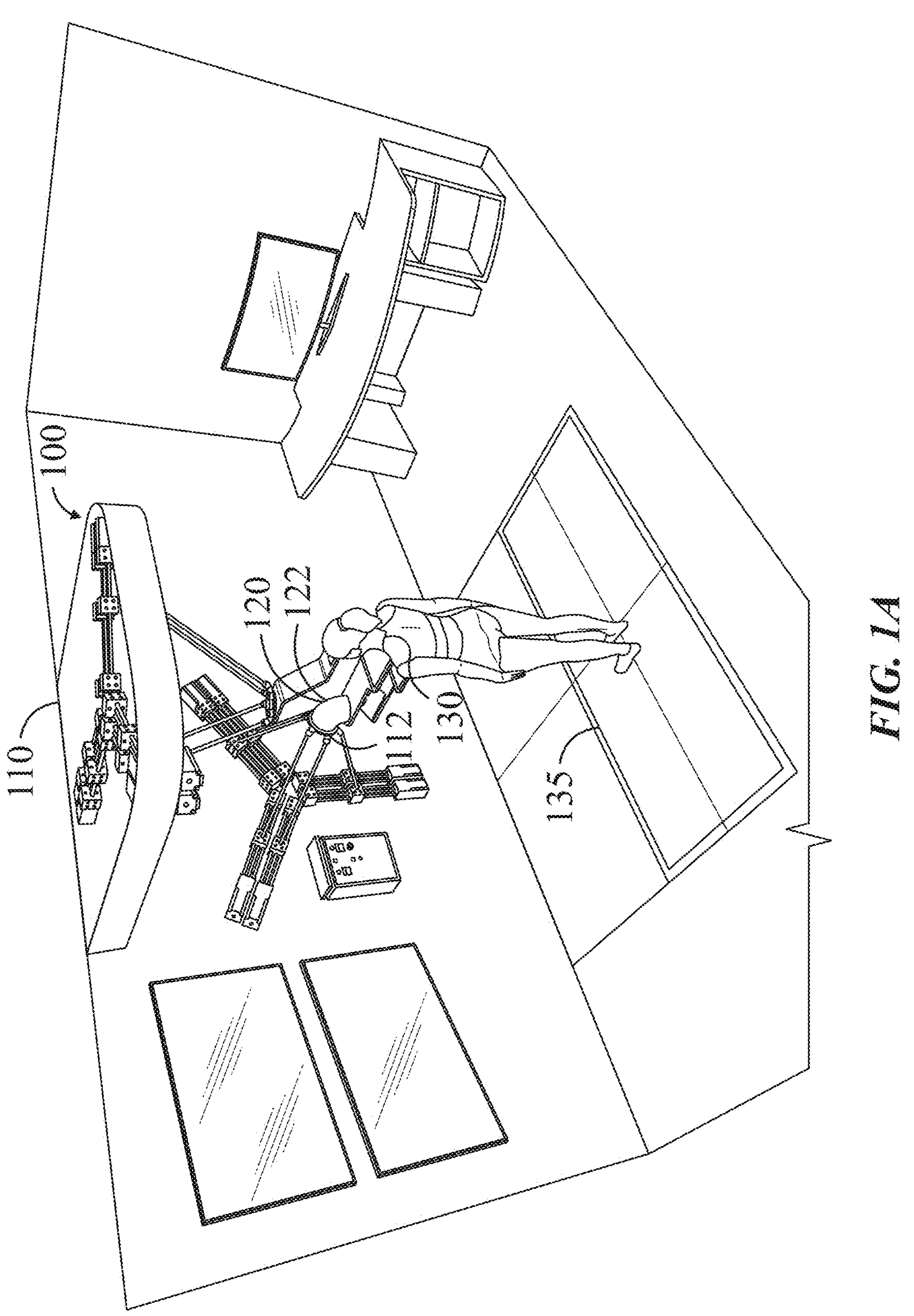
FIG. 1A is a perspective view of the electronically steerable x-ray imaging system showing the system in a clinical scanning environment, according to some embodiments.

The specific details of the single embodiment or variety of embodiments described herein are set forth in this application. Any specific details of the embodiments described herein are used for demonstration purposes only, and no unnecessary limitation(s) or inference(s) are to be understood or imputed therefrom.

Before describing in detail exemplary embodiments, it is noted that the embodiments reside primarily in combinations of components related to particular devices and systems. Accordingly, the device components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

The following detailed description relates to an electronically steerable x-ray imaging system that may be configured to direct x-ray beams toward an imaging target with controllable directionality and focus. The system may incorporate an x-ray beam generator capable of emitting radiation in a low-energy range suitable for soft tissue imaging and may include beam steering elements positioned along the x-ray path to facilitate programmable deflection. A sensor array may be used to detect x-ray data after transmission through the imaging target, and a computer system may process the collected data to reconstruct an image. The image reconstruction may be performed using an iterative algorithm adapted to enhance tumor visibility and reduce noise, particularly in dense or heterogeneous tissue environments. The system may be used to obtain detailed diagnostic images of internal anatomical structures, such as human breast tissue, while minimizing radiation exposure and enabling detection of small lesions or abnormalities.

An electronically steerable x-ray imaging system may include an electronically steerable x-ray source comprising an x-ray beam generator configured to emit an x-ray beam. The x-ray beam generator may produce radiation in an energy range between approximately 30 keV and 50 keV, a range typically considered suitable for imaging soft biological tissue such as human breast tissue. This energy range may provide adequate penetration depth and differential attenuation among various tissue structures while minimizing ionizing exposure to the surrounding anatomy. The electronically steerable nature of the x-ray source may permit the emitted beam to be redirected in real-time across multiple angular orientations with respect to a stationary imaging target.

The x-ray beam generator may be positioned within a housing or gantry structure that includes a robotic or electromechanical actuation mechanism. The actuation mechanism may include one or more servo motors, stepper motors, or piezoelectric elements, configured to alter the beam's angular position in either discrete increments or continuous trajectories. Steering commands may originate from a controller or computing system that evaluates tissue density, imaging priority zones, or operator instructions to select an appropriate beam orientation. In one example, a delta-robot or SCARA-style arm may serve as a carrier for the x-ray beam generator, allowing for programmable motion paths within a defined imaging envelope. The x-ray beam may be collimated or shaped prior to exiting the housing using a programmable aperture, slit, or conical collimator.

A sphere array may be positioned in the beam path between the x-ray beam generator and an imaging target. The sphere array may function to enable electronic steering of the x-ray beam by deflecting its path via physical interactions with materials of different x-ray refractive indices. In some embodiments, the sphere array may be constructed from a plurality of Janus spheres, wherein each Janus sphere comprises two hemispherical regions formed from distinct materials. One hemisphere may be composed of a high atomic number material (e.g., tungsten, tantalum), while the other hemisphere may be formed from a lower atomic number material (e.g., beryllium, plastic polymer). The contrast in refractive index may cause incident x-ray photons to undergo angular deviation depending on the orientation of each Janus sphere in the array.

The Janus sphere array may be mounted in a substrate or flexible membrane that permits positional adjustment of the spheres for active control over the deflection angle. A motorized stage, electrostatic field generator, or magnetic actuator may modify the angular alignment of the Janus spheres in real-time, thereby modifying the resulting x-ray beam path as it exits the array. This configuration may support high-precision beam steering without the need for moving the entire x-ray source, allowing for reduced mechanical complexity and increased imaging responsiveness. Beam trajectory calibration may be performed by using feedback from a downstream sensor array to iteratively adjust sphere alignment until a target region receives maximum intensity. In one configuration, the Janus spheres may be arranged in a planar or slightly curved array to conform to the geometry of the imaging region.

The imaging target may be configured to receive the x-ray beam as it exits the Janus sphere array. The imaging target may include either human breast tissue or a breast phantom designed to replicate the anatomical and radiological properties of breast structures. The phantom may include variable-density layers, embedded tumor simulants, or microcalcification inclusions that allow for system calibration and testing under simulated clinical conditions. In clinical use, the imaging target may be positioned within a compression device or guided support fixture to ensure positional stability and uniform imaging geometry. The x-ray beam may be directed at various depths, angles, or regions of the imaging target to generate a dataset suitable for volumetric or planar reconstruction.

A sensor array may be positioned relative to the imaging target such that it receives x-ray data after the beam has penetrated the tissue. The sensor array may include multiple solid-state detectors such as cadmium telluride (CdTe), amorphous silicon, or scintillator-coupled photodiodes. Each detector element may convert incident x-ray photons into analog or digital signals corresponding to the local attenuation of the beam. The array may be configured in a flat, arcuate, or full-enclosure geometry, depending on the desired imaging field of view. Signals collected by the sensor array may be transmitted to a computer system for storage, filtering, and image reconstruction.

The computer system may include a processor configured to receive the plurality of x-ray data from the sensor array and reconstruct an image inferred from the data. The reconstruction process may implement a Multiplicative Algebraic Reconstruction Technique (MART), which iteratively updates the estimated image based on the comparison between measured and simulated projections. Each iteration may adjust voxel intensities to reduce the discrepancy between the measured transmission profile and the current image estimate. The MART algorithm may prioritize beam paths with higher signal-to-noise ratios or those that intersect with diagnostically significant regions. Intermediate reconstruction outputs may be evaluated and used to update beam steering parameters to refine image fidelity in real time.

The reconstructed image may be optimized to enhance visibility of anatomical structures such as tumors, ducts, lobules, and calcifications. The processor may apply digital filtering, histogram equalization, or gradient-based edge enhancement techniques to emphasize structural detail. Noise may be minimized through multi-pass smoothing algorithms, statistical denoising, or low-dose compensation functions built into the MART framework. In addition, contrast-to-noise ratio (CNR) and modulation transfer function (MTF) metrics may be evaluated during reconstruction to guide algorithmic parameter selection. The resulting image may be rendered in 2D or 3D formats suitable for diagnostic review, interventional planning, or quantitative analysis.

The computer system may also be configured to adjust one or more steering parameters and one or more imaging parameters based on a tissue density and structure. Steering parameters may include angular deflection of the beam, exposure duration, pulse repetition frequency, and spatial scanning trajectory. Imaging parameters may include voxel size, sampling resolution, and reconstruction filter weights. Initial tissue density information may be derived from prior scans, scout images, or machine learning estimators trained on population data. Structural features may be determined by edge detection or segmentation techniques applied to preliminary images and may trigger localized beam steering to increase sampling in areas of suspected pathology.

In another embodiment, the electronically steerable x-ray source may be capable of adjusting a direction, an intensity, and a focus of the x-ray beam in real time. Direction may refer to angular orientation of the beam relative to a fixed coordinate frame; intensity may refer to beam power or photon flux; focus may refer to beam width or spot size at a given distance from the source. Adjustment may be executed via motorized actuators, electromagnetic deflection coils, or dynamic collimation devices. Feedback from the sensor array or from external imaging modalities (e.g., ultrasound, MRI) may guide these adjustments during an active scan. Real-time control may support dynamic tracking of moving targets, adaptive exposure compensation, or targeted imaging of suspicious regions.

In one example, the electronically steerable x-ray imaging system may be used to acquire multiple projections from different angles without requiring physical rotation of the source or imaging target. These projections may be used to reconstruct tomographic or 3D images of breast tissue, offering improved visualization over traditional 2D mammography. The dynamic beam steering and programmable deflection may allow for flexible acquisition protocols such as sparse-angle CT, limited-angle tomography, or region-of-interest scans. Imaging times may be reduced due to the reduced mechanical movement and intelligent data selection inherent to MART. As a result, clinicians may obtain diagnostic-quality images in less time and with fewer patient repositioning steps.

The electronically steerable x-ray imaging system may also support a method for detecting a tumor present in human breast tissue. The method may begin with positioning a breast within an imaging area in optical view of the electronically steerable x-ray source and the sensor array. The x-ray beam generator may then emit a beam that is focused on an imaging target via the Janus sphere array. The deflection angle of the x-ray beam may be adjusted in real time based on tissue density and one or more structural features. These steps may be executed automatically, semi-autonomously, or under direct user control.

Once the beam has passed through the breast tissue, the sensor array may collect a plurality of x-ray data corresponding to differential attenuation at various tissue depths and densities. This data may be digitized and transmitted to the computer system for analysis. The system may reconstruct an image from the x-ray data using the MART algorithm and output the image to a diagnostic workstation or display. Tumors, if present, may appear as high-contrast regions due to localized attenuation patterns. The method may be repeated for multiple angles or may include adaptive re-scanning of suspicious regions to increase diagnostic confidence.

The sensor array may be capable of detecting tumors ranging in size between about 2 and 4 millimeters, depending on detector resolution, beam focus, and reconstruction settings. Tumors of this size may not be visible in conventional mammography due to tissue overlap or insufficient resolution. By combining beam focusing, programmable deflection, and MART image reconstruction, the system may isolate tumor signatures from background tissue and noise. The use of low-dose x-rays may permit frequent imaging for high-risk populations without exceeding recommended radiation exposure levels. This configuration may also be adapted for longitudinal studies, intervention planning, or follow-up imaging after treatment.

As used herein, the term "imaging target" refers to any biological or simulated structure that is positioned to receive the x-ray beam emitted from the electronically steerable x-ray source. The imaging target may include a portion of human breast tissue, an organ, or other biological tissue of interest in which tumor detection, density analysis, or structural imaging is performed. In some embodiments, the imaging target may also include a breast phantom, which is a synthetic construct that replicates the mechanical, radiological, and anatomical properties of the human breast for calibration, testing, or training purposes. The imaging target serves as the medium through which the x-ray beam passes prior to reaching the sensor array, thereby determining the measured x-ray attenuation characteristics that inform image reconstruction. By defining this term broadly, imaging targets may encompass both live anatomical tissues and synthetic analogs used for simulation or system verification.

As used herein, the term "MART algorithm" refers to a computational reconstruction method known as the Multiplicative Algebraic Reconstruction Technique, implemented by the processor of the computer system. The MART algorithm iteratively refines an estimated image of internal tissue structure by applying multiplicative correction factors derived from discrepancies between measured and simulated x-ray projections. Each iteration adjusts voxel attenuation coefficients proportionally to the ratio of observed and predicted transmission data, allowing convergence toward a high-fidelity reconstruction. MART may be executed in two or three dimensions and is particularly suited for cases where limited-angle projection data or sparse sampling is available. In this context, the MART algorithm enables the electronically steerable x-ray system to reconstruct detailed internal representations of tissue morphology while minimizing noise and computational overhead.

As used herein, the term "x-ray data" refers to the collection of digital information generated by the sensor array after the x-ray beam has passed through the imaging target. The x-ray data may include pixel-based intensity measurements, attenuation coefficients, or transmission ratios recorded at multiple angles and energy levels. Each data element corresponds to the amount of x-ray energy received at a specific detector element, collectively forming a projection dataset. The x-ray data may be stored in raw, pre-processed, or normalized form, and may be formatted for compatibility with reconstruction algorithms such as MART. The data serves as the primary input for computational image generation and may also be used to derive secondary imaging metrics, such as contrast, signal-to-noise ratio, or tissue density estimation.

As used herein, the term "tissue density" refers to the mass per unit volume or the x-ray attenuation coefficient of biological or synthetic material within the imaging target. Tissue density determines the degree to which x-ray photons are absorbed and scattered as they pass through the target, directly influencing the resulting intensity patterns captured by the sensor array. Denser tissues, such as fibroglandular regions of the breast or calcified structures, exhibit greater x-ray attenuation than fatty or soft tissues, creating contrast in the reconstructed image. Measuring and adapting to tissue density is essential for accurate beam steering, exposure control, and image optimization, as it allows the system to dynamically adjust beam energy and intensity in real-time. The computer system may utilize local tissue density data to tune the steering parameters of the x-ray beam and improve diagnostic resolution while minimizing patient dose.

As used herein, the term "Janus sphere array" refers to a collection of microspheres or engineered spherical elements having dual-material or dual-surface compositions that facilitate electronic steering of x-ray beams. Each Janus sphere may possess two hemispherical regions with differing refractive, magnetic, or electrostatic properties, enabling selective deflection or modulation of incident x-ray photons. When organized into an array, the Janus spheres may respond to applied electromagnetic or electrostatic fields to alter the deflection angle of the x-ray beam in real-time. The Janus sphere array thus functions as a tunable x-ray steering mechanism, allowing precise control over beam direction, focus, and distribution without requiring mechanical repositioning of the x-ray source. This configuration enhances imaging flexibility, reduces motion artifacts, and enables adaptive targeting of regions of interest within the imaging target.

As used herein, the term "imaging target" refers to any biological or simulated material positioned within the imaging field to receive the x-ray beam emitted from the electronically steerable x-ray source. The imaging target may include human breast tissue, other soft or dense tissue, or a synthetic phantom designed to replicate biological tissue properties. In some embodiments, the imaging target may include calibration or test phantoms used during simulation or verification procedures. The imaging target determines the attenuation, scattering, and transmission characteristics of the x-ray beam as it propagates through the material. By defining the imaging target in this manner, the term encompasses both live anatomical tissue and artificial analogs used for testing or modeling.

As used herein, the term "electronically steerable x-ray source" refers to a radiation-emitting assembly configured to produce an x-ray beam whose direction, intensity, and focus may be modified through electronic control or robotic mechanical repositioning. The electronically steerable x-ray source may include an x-ray beam generator, a focusing structure, and a steering subsystem operatively coupled to the Janus sphere array. In some embodiments, the source may be configured to emit x-rays within an energy range of 30-50 keV, and its emission profile may be modulated in real-time based on feedback from the sensor array or computing system. The electronically steerable design allows precise control of the x-ray trajectory, exposure level, and imaging region, enabling dynamic targeting of tissue regions of interest. The term is intended to cover any x-ray source capable of electronic deflection or modulation of its beam path.

[As used herein, the term "Janus sphere array" refers to a set of engineered spherical elements having two or more hemispherical regions with differing electromagnetic, optical, or electrostatic properties. The Janus spheres may be arranged in an array or lattice structure along the x-ray beam path, enabling controlled deflection or focusing of x-ray photons in response to applied electromagnetic fields. The array may operate by adjusting the relative orientation or polarization of the spheres to achieve beam steering at predetermined angles. The Janus sphere array provides fine, rapid beam direction control without requiring mechanical actuation, allowing the system to steer the x-ray beam with high spatial precision. The term includes both micro- and macro-scale configurations that achieve electronically controllable photon deflection.

As used herein, the term "sensor array" refers to a grid or matrix of x-ray detectors positioned to capture transmitted radiation after it passes through the imaging target. Each detector element may convert incident x-ray photons into electrical signals representing localized intensity or attenuation values. The sensor array may comprise semiconductor, scintillator, or digital flat-panel detectors, and may be configured to collect data at multiple angular positions. The resulting signals are processed into a plurality of x-ray data that represent the tissue's internal attenuation profile. The term "sensor array" encompasses both static and movable detector configurations, including arrays integrated with tomographic or scanning systems.

As used herein, the term "x-ray data" refers to the digital or analog information acquired by the sensor array after the x-ray beam has interacted with the imaging target. The x-ray data may include measured intensity values, attenuation coefficients, or projection datasets corresponding to multiple beam orientations. Each data point reflects the cumulative absorption and scattering encountered along a specific beam path. The x-ray data may be stored in memory for further processing, formatted as projection matrices, or streamed directly to the processor for reconstruction using the MART algorithm. The term broadly encompasses raw, processed, or normalized datasets derived from the imaging system's sensing operations.

As used herein, the term "tissue density" refers to the relative mass per unit volume or attenuation coefficient of a tissue region as it affects x-ray absorption and transmission.

Differences in tissue density determine how the x-ray beam interacts with different regions of the imaging target, influencing contrast and visibility in the reconstructed image. Dense tissues, such as fibroglandular or calcified regions, attenuate x-rays more strongly than less dense tissues such as adipose regions. Monitoring and adapting to tissue density enables real-time modulation of beam intensity, exposure time, and deflection angle. The system may dynamically adjust imaging parameters based on tissue density variations to improve image clarity and reduce patient dose. The term may encompass both actual biological density and computationally derived attenuation density estimates.

As used herein, the term “MART algorithm” refers to the Multiplicative Algebraic Reconstruction Technique implemented by the computer system to reconstruct a digital image from x-ray data. The MART algorithm iteratively refines an image estimate by comparing simulated projections with measured x-ray data and updating voxel attenuation coefficients via multiplicative correction factors. Each iteration adjusts the image matrix to minimize discrepancies and improve fidelity to measured projections. The algorithm may operate in two-dimensional or three-dimensional space and can be configured for varying projection geometries or limited-angle datasets. The MART algorithm may also integrate regularization, noise suppression, or adaptive weighting techniques to accelerate convergence and improve image resolution.

As used herein, the term “multiplicative correction factor” refers to a scaling coefficient applied to each voxel or image element during an iteration of the MART algorithm. The factor is derived from the ratio between measured and simulated projection values for beam paths intersecting the voxel. The correction factor modifies voxel values multiplicatively to progressively align the reconstructed image with the actual x-ray measurements. Correction factors may be normalized, averaged, or constrained to prevent overcorrection and maintain numerical stability. The term includes both explicit correction matrices and computationally equivalent scaling operations used in iterative reconstruction algorithms.

As used herein, the term “reconstructed image” refers to a two- or three-dimensional digital representation of the internal structure of the imaging target generated from the plurality of x-ray data. The reconstructed image is composed of pixel or voxel intensity values that correspond to tissue attenuation coefficients or density variations. It may be displayed as cross-sectional slices, volumetric renderings, or projection images on a monitor or diagnostic display. The reconstructed image provides a visual and analytical basis for identifying regions of interest, including potential tumors or abnormal tissue formations. The term includes both intermediate and final outputs of the reconstruction process prior to optimization or enhancement.

As used herein, the term “optimization” refers to the set of computational processes performed by the computer system to enhance the quality, contrast, or diagnostic utility of the reconstructed image. Optimization may involve filtering, contrast adjustment, noise suppression, segmentation, or adaptive histogram equalization. The process may improve the signal-to-noise ratio (SNR) and contrast-to-noise ratio (CNR) in regions containing diagnostic detail. Optimization may also reduce image artifacts that arise during acquisition or reconstruction. The term broadly encompasses any image enhancement or correction process that improves interpretability or quantitative accuracy of the reconstructed data.

As used herein, the term “adaptive beam control” refers to the system’s ability to dynamically adjust the x-ray beam’s intensity, energy, focus, or direction in response to feedback data obtained during imaging. Such feedback may include real-time measurements of tissue density, detected scatter, or reconstruction quality metrics. The adaptive beam control subsystem may utilize the Janus sphere array, x-ray beam generator, and computing system in an integrated feedback loop. Adjustments may occur continuously during a scan or between sequential imaging frames. This functionality enables the imaging system to improve focus, reduce unnecessary exposure, and maintain consistent image quality across heterogeneous tissues.

As used herein, the term “scattering reduction steering” refers to an electronic beam steering process that minimizes secondary x-ray scatter detected by the sensor array, aided by knowing where each x-ray beam is directed. The electronically steerable x-ray source and Janus sphere array cooperate to adjust beam incidence angles and collimation patterns based on measured or predicted scattering behavior. By reducing or even using scatter, the system enhances image contrast and improves reconstruction accuracy. The process may include iterative steering adjustments and feedback correction based on detector input. The term encompasses both proactive beam shaping and reactive compensation strategies to suppress unwanted x-ray dispersion.

As used herein, the term “tumor detection” refers to the identification of regions within the reconstructed image that exhibit radiological characteristics consistent with neoplastic or abnormal tissue growth. Tumor detection may be accomplished through algorithmic segmentation, contrast thresholding, contrast agents, or supervised computational analysis. The process may include the evaluation of attenuation patterns, local texture, and density gradients to distinguish potential tumor regions from surrounding tissue. Detected regions may be highlighted, annotated, or quantified for clinical interpretation. The term encompasses both automated and manual detection techniques performed on reconstructed or optimized images.

As used herein, the term “computer system” refers to one or more hardware and software components configured to execute the MART algorithm, control beam steering, process x-ray data, and generate the reconstructed image. The computer system may include a processor, memory, storage device, display, and data interface interconnected via a system bus. Software modules may include preprocessing, reconstruction, optimization, and user interface subsystems. The processor may execute machine-readable instructions stored in memory to perform the imaging operations described herein. The term may encompass local computing devices, networked processing systems, or distributed computational architectures.

As used herein, the term “deflection angle” refers to the measurable geometric angle at which the x-ray beam is redirected from its nominal optical axis by the Janus sphere array or related steering mechanism. The deflection angle may be dynamically varied during imaging to target specific tissue regions or to optimize image coverage. The angle may be controlled electronically through modulation of electric or magnetic fields applied to the Janus spheres. The system may record and adjust deflection angles in real-time to maintain consistent focus and minimize aberrations. The term includes both static and variable steering angles implemented by the electronically steerable x-ray source.

Figure 1B:
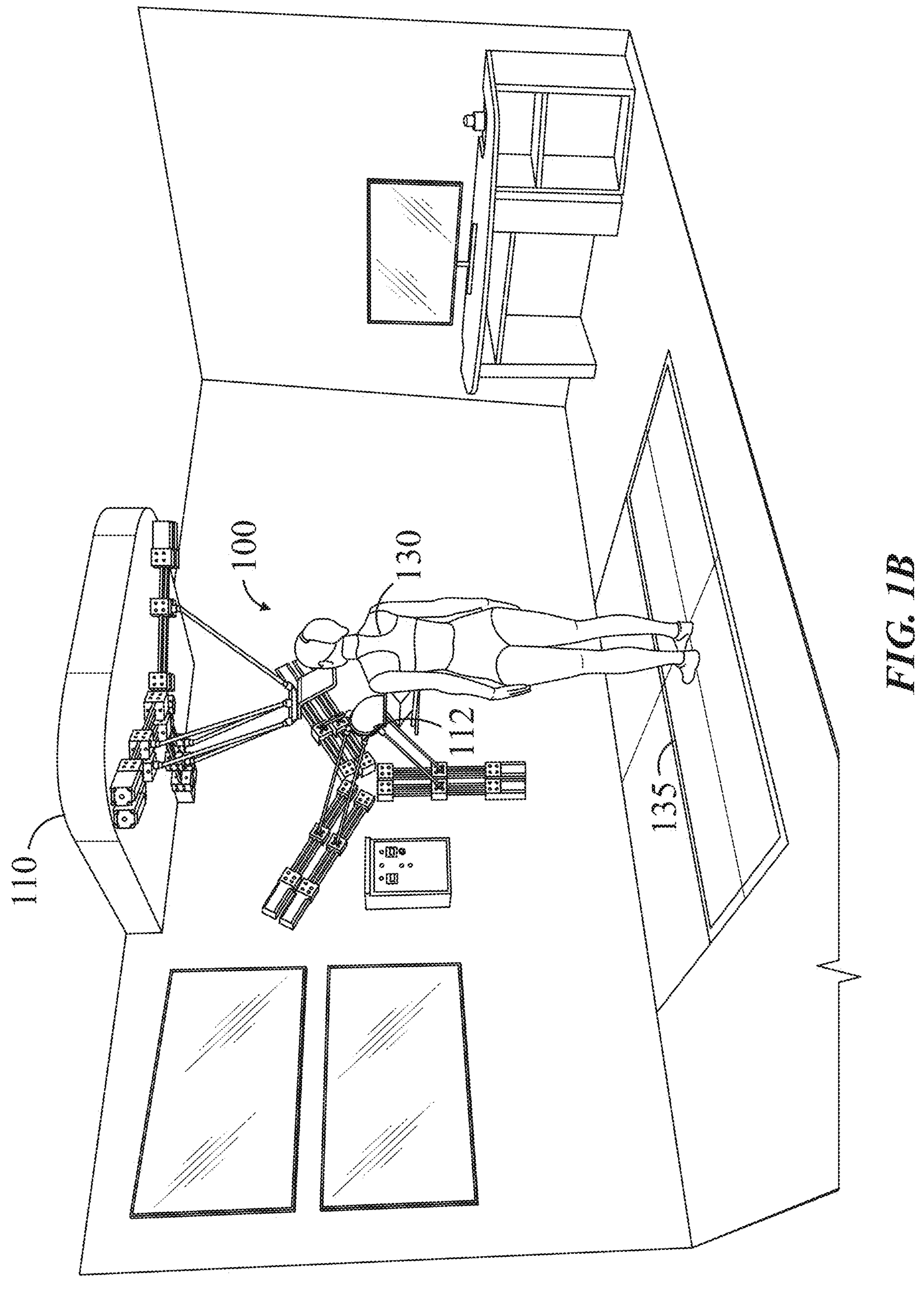
FIG. 1B is a perspective of the imaging system illustrating the beam path between the x-ray source and the sensor array during imaging, according to some embodiments.
Figure 1C:
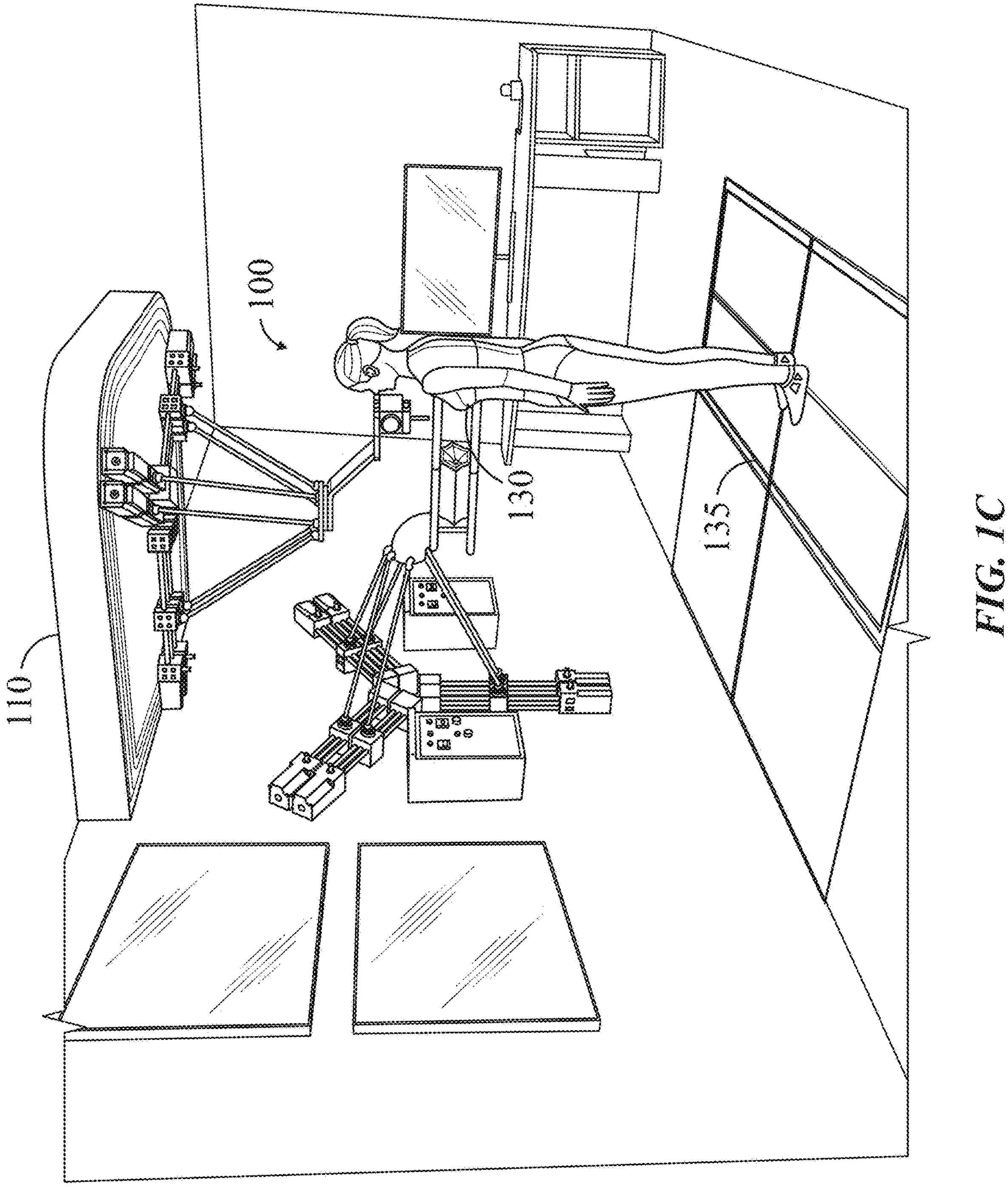
FIG. 1C is a perspective of the imaging system showing the alignment between the x-ray beam generator, the imaging target, and control workstation, according to some embodiments.

FIGS. 1A, 1B, and 1C depict perspective views of an electronically steerable x-ray imaging system 100 configured to facilitate diagnostic imaging of breast tissue in a clinical or simulated environment. The system 100 includes an electronically steerable x-ray source 110 suspended above an imaging area defined by a patient platform 135. The electronically steerable x-ray source 110 may comprise a programmable robotic assembly that allows for three-dimensional positioning of an x-ray beam generator 112 with respect to an imaging target 130. The patient, or in some cases a breast phantom used for calibration or simulation, may be positioned upright on the platform 135 within the imaging field of view. The beam emitted by the x-ray beam generator 112 may be directed downward toward the imaging target 130 and further manipulated by beam-steering elements located along the beam path.

The x-ray beam generator 112 may emit an x-ray beam with an energy level within a range between approximately 30 and 50 keV, a range that is commonly used for imaging soft biological tissues such as human breast structures. The direction and focus of the x-ray beam may be adjusted in real time by mechanical or electronic actuation of the robotic linkage that supports the x-ray source 110. Steering may be performed by pivoting the source about one or more axes, translating it laterally across a predefined workspace, or adjusting its height relative to the imaging platform 135. These movements may be executed under the control of a computer system 150 that interprets steering instructions derived from tissue characteristics, imaging presets, or user-defined commands.

Interposed between the x-ray beam generator 112 and the imaging target 130 is a sphere array 120 configured to modify the path of the x-ray beam. The sphere array 120 may be formed from a plurality of Janus spheres 122 that are selectively orientable and composed of two distinct materials with different x-ray refractive indices. These Janus spheres 122 may serve to electronically steer the x-ray beam by producing angular deflection when the beam passes through their material interface. The physical orientation of the Janus spheres 122 may be adjusted either manually or by automated means, such as electrostatic or magnetic actuation, to change the effective deflection angle imposed on the beam. In some configurations, the Janus spheres 122 may be housed within a structured enclosure or mounted on a tiltable platform that rotates to align the array with the desired beam direction.

The imaging target 130 may include either an actual human breast or a breast phantom comprising tissue-equivalent materials with embedded features simulating tumors or microcalcifications. The platform 135 beneath the target may include visual alignment markings or adjustable supports to ensure consistent positioning across multiple imaging sessions. During operation, the x-ray beam may be directed toward various portions of the imaging target 130 to capture different anatomical planes or volumes. The beam steering provided by the combination of the x-ray source 110 and the sphere array 120 may permit angular imaging without physically moving the target itself, thereby improving patient comfort and workflow efficiency. Depending on the procedure, the imaging target 130 may be compressed, immobilized, or left in a free-hanging pendant position based on the anatomical zone of interest.

A sensor array 140 is positioned opposite or adjacent to the imaging target 130 and configured to collect a plurality of x-ray data 116 after the beam has passed through the tissue. The sensor array 140 may include linear or planar arrays of x-ray detectors, such as amorphous silicon panels, CMOS sensors, or scintillator-photodiode combinations. Each detector element within the sensor array 140 may generate an analog or digital signal representing localized x-ray attenuation. These signals may be used to construct two- or three-dimensional projection images or tomographic datasets. In certain configurations, the sensor array 140 may also capture scattered x-ray photons to improve image reconstruction in low-dose or high-density scenarios.

The x-ray data 116 collected by the sensor array 140 may be transmitted to a computer system 150 comprising a processor 152 and associated memory and control logic. The processor 152 may be configured to execute a reconstruction algorithm, such as a Multiplicative Algebraic Reconstruction Technique (MART), to reconstruct an image inferred from the x-ray data 116. The MART algorithm may iteratively update voxel or pixel values based on the difference between measured detector signals and expected values computed from the current reconstruction. During this process, the system 100 may optimize tumor visibility and minimize noise, including scatter-induced artifacts, motion blurring, or electronic interference. The reconstructed image may be displayed in real-time on one or more monitors 162 positioned near a user workstation 160.

As shown in FIGS. 1A through 1C, the user workstation 160 may include a display monitor 162, keyboard, and control interface that allow an operator to initiate scans, select beam steering parameters, review images, or adjust reconstruction settings. The workstation 160 may also present live feedback during a scan, enabling the operator to modify beam orientation or exposure settings in response to interim results. Additional screens may display diagnostic data, such as tissue density maps, image histograms, and reconstruction convergence metrics. The system 100 may be network-connected for integration into larger medical imaging systems or electronic medical records platforms. Collectively, FIGS. 1A, 1B, and 1C illustrate the spatial arrangement, hardware architecture, and functional interactions among the electronically steerable x-ray source 110, the imaging target 130, the sensor array 140, and the computer system 150.

Figure 2:
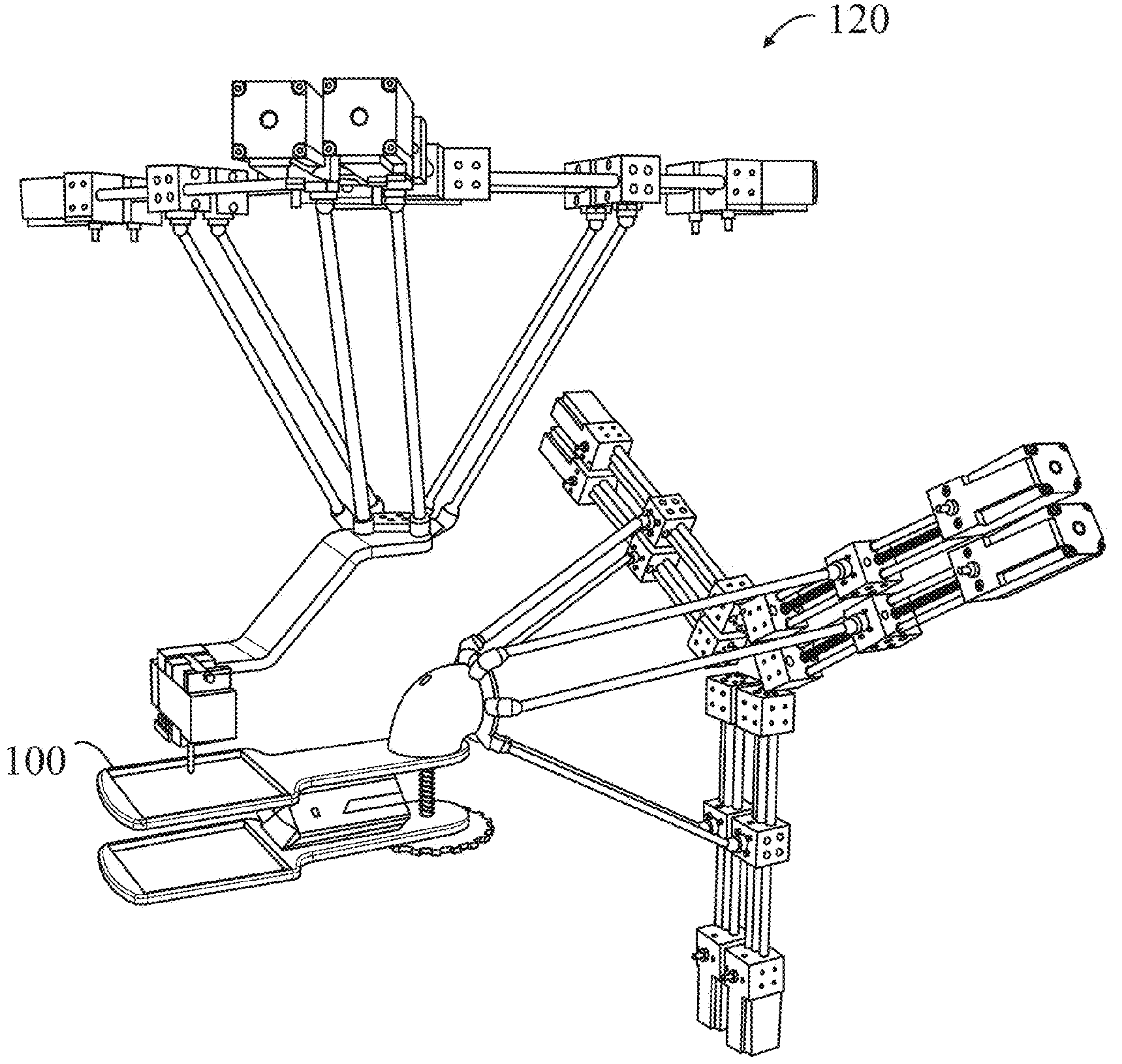
FIG. 2 is an internal view of the x-ray imaging system illustrating the mechanical arrangement of the x-ray beam generator, Janus sphere array, and imaging platform, according to some embodiments.

FIG. 2 illustrates the inner configuration of the electronically steerable x-ray imaging system 100, showing the mechanical linkage and spatial arrangement between the x-ray beam generator 112, the electronically steerable x-ray source 110, and the imaging components positioned beneath. The electronically steerable x-ray source 110 includes a delta-style robotic armature comprising a central platform and three symmetric actuator arms, each connected to a top-mounted control frame. The platform supports the x-ray beam generator 112, which is mounted to the lower portion of the robotic linkage via an adjustable gimbal or rotational joint. The actuator arms may include parallel linkages that maintain angular stability and allow for smooth translation and tilting of the x-ray beam generator 112 within a predefined working volume. Movement of the robotic arms may be driven by stepper motors or servo motors housed in the control frame and may be coordinated through motion control software executed by the computer system 150.

Positioned directly beneath the x-ray beam generator 112 is a deflection system including a Janus sphere array 120 mounted within a beam-directing structure. The beam emitted from the x-ray beam generator 112 travels downward through the Janus sphere array 120, which is supported by an enclosure or frame allowing angular and lateral adjustments. The Janus spheres 122 within the array may consist of bifacial hemispheres made from materials of differing x-ray refractive indices, such as tungsten and acrylic, or other combinations suitable for differential beam bending. The deflection of the x-ray beam 114 occurs as the beam passes through the interface between the two hemispheres of each Janus sphere 122, resulting in a change in trajectory that may be controlled by modifying the physical orientation of the array or the individual spheres themselves. The beam may be collimated prior to entering the Janus sphere array 120, and optionally re-shaped or filtered before reaching the imaging target 130.

The imaging target 130 is shown beneath the beam path and may include breast tissue or a tissue-equivalent breast phantom positioned between two horizontal support plates. These plates may function as an adjustable compression or stabilization fixture and may be mounted to a structural base platform 135. The target zone is aligned with the vertical axis of the electronically steerable x-ray source 110 and the beam path exiting from the Janus sphere array 120. The imaging target 130 may be positioned using vertical alignment guides or may rest on a marked scanning mat to ensure consistent registration between the imaging area and the beam delivery system. Optionally, actuators or fine-thread lead screws may be included in the platform 135 to raise, lower, or tilt the imaging target 130 for alignment with various beam orientations during scanning.

Also visible in FIG. 2 is a secondary mechanical armature extending laterally from the imaging region. This may represent a mounting system for additional sensor modules or a support system for the sensor array, not shown in this figure but positioned to detect the x-ray data after beam penetration. The modular design allows integration of beam monitoring systems, safety interlocks, and calibration detectors to ensure that the beam intensity, focal region, and trajectory are within operational thresholds during a scan. The positioning of the components in FIG. 2 provides a clear view of the kinematic flexibility of the x-ray source 110, the function of the Janus sphere array 120, and the anatomical alignment zone beneath the source.

The configuration shown in FIG. 2 supports full electronic and mechanical steering of the x-ray beam without requiring movement of the imaging target. By adjusting both the robotic arm holding the x-ray beam generator and the deflection angle of the Janus sphere array 120, the system 100 may target specific tissue regions, sweep across predefined paths, or concentrate imaging resolution to zones of interest. This flexibility supports multiple imaging protocols, including full-field scans, partial-angle acquisitions, or dynamic response imaging triggered by tissue feedback. The inner configuration enables real-time control of x-ray delivery and supports integration with the computing and sensor subsystems responsible for image reconstruction and optimization.

Figure 3A:
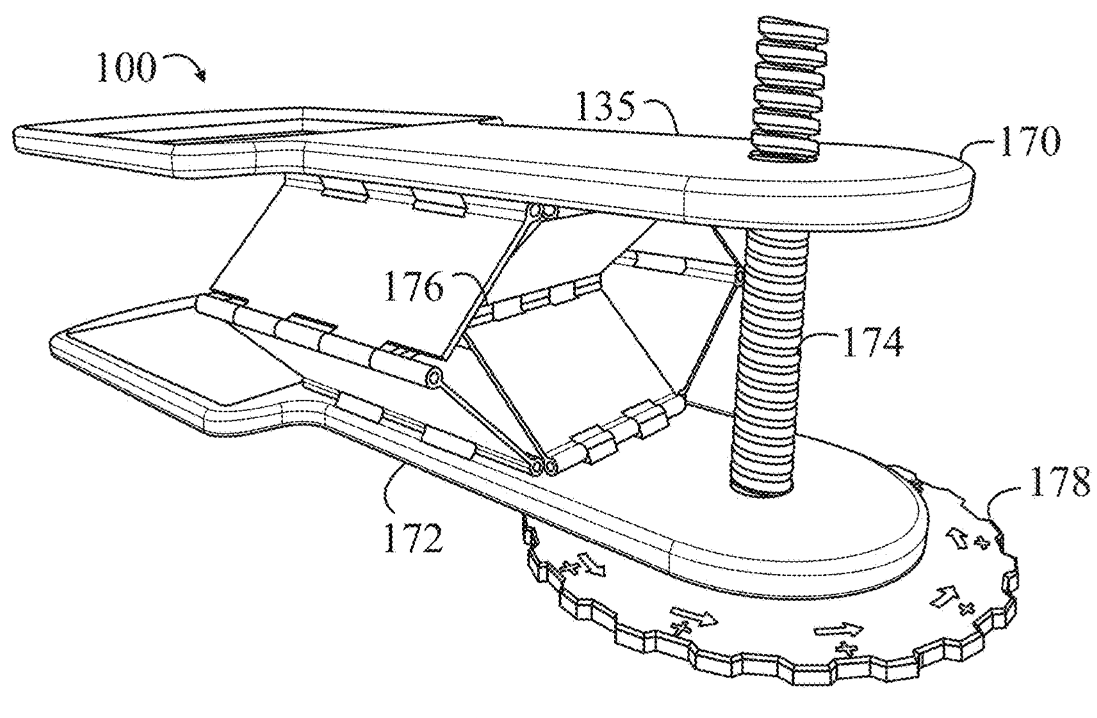
FIG. 3A is a perspective view of a vertically adjustable imaging platform configured to support the imaging target during scanning, according to some embodiments.
Figure 3B:
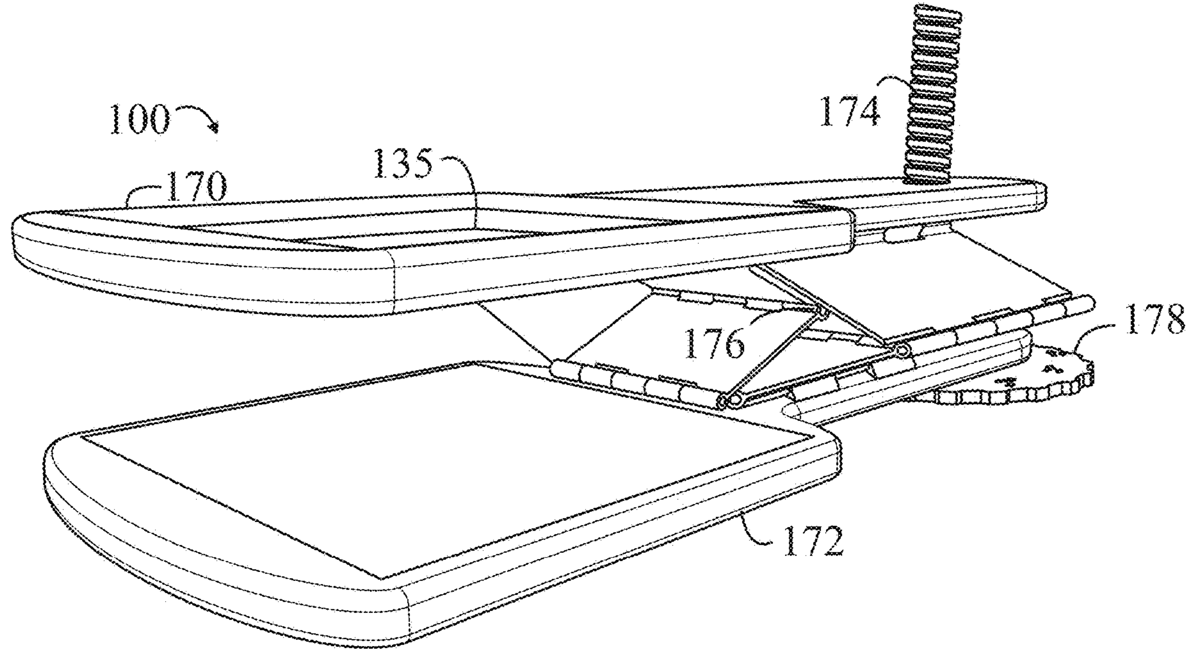
FIG. 3B is a perspective view of the imaging platform showing the structural components used for target alignment and stabilization, according to some embodiments.

FIGS. 3A and 3B illustrate perspective views of a portion of the x-ray imaging system 100, showing the structural configuration used to support, align, and stabilize an imaging target positioned between opposing surfaces of an imaging platform 135. The imaging platform 135 includes an upper support plate 170 and a lower support plate 172, which may be vertically adjustable relative to one another via a central threaded guide shaft 174. The guide shaft 174 may be rotated manually or by motorized control to raise or lower the upper support plate 170 with respect to the lower support plate 172, thereby accommodating different tissue volumes or compression settings. A plurality of mechanical linkages 176 are shown extending diagonally between the support plates 170 and 172, which may serve as scissor mechanisms or telescoping braces to guide the platform's vertical motion.

In FIG. 3A, the lower surface of the imaging platform 135 is mounted on a rotary base plate 178, which includes multiple rotational arrows indicating the potential for angular adjustment. The rotary base plate 178 may allow the entire imaging platform 135 to be rotated around a central axis, enabling angular repositioning of the imaging target 130 beneath the electronically steerable x-ray source 110. This configuration may be particularly useful for acquiring multi-angle projections or for targeting specific tissue regions based on anatomical orientation. The rotation may be indexed in fixed increments or adjusted continuously and may be locked in place using mechanical detents or magnetic couplings to maintain positional stability during imaging.

FIG. 3B shows the imaging platform 135 from an alternate perspective, highlighting the overall geometry of the support plates 170 and 172. In this view, the upper support plate 170 may include a cutout or recessed cavity to accommodate or position the breast or phantom structure representing the imaging target 130. The support plates 170 and 172 may be formed from low-density, x-ray transparent materials such as polycarbonate or carbon fiber composites, allowing the x-ray beam 114 to pass through with minimal attenuation or scattering. Each plate may include attachment points, recessed grooves, or silicone interfaces to cradle the target and reduce motion during scanning. In some embodiments, radiopaque markers or fiducial grids may be embedded into one or both plates to assist with spatial registration during image reconstruction.

The linkage arms 176 shown in both FIG. 3A and FIG. 3B may be spring-loaded or motorized to provide uniform pressure during vertical adjustment. This vertical adjustability allows the imaging system 100 to accommodate patients with varying anatomical presentations and compression pain thresholds, or to simulate different levels of tissue compression when using phantoms for calibration and testing. The platform's geometry may also be configured to integrate with external position tracking systems, such as optical markers or electromagnetic fiducials, which can be used to precisely register the imaging target 130 relative to the x-ray beam generator and sensor array 140. Additionally, FIG. 3B shows the underside of the lower support plate 172 as being flat and open, permitting proximity placement of the sensor array for maximum signal capture efficiency.

The mechanical configuration illustrated in FIGS. 3A and 3B supports both manual and automated imaging workflows, enabling repeatable alignment of the imaging target 130 with the beam path defined by the electronically steerable x-ray source 110. The support structure may be modular, permitting removal, replacement, or cleaning of the platform components between imaging sessions. In some cases, alternate inserts or adapter plates may be installed on the upper support plate 170 to accommodate targets of different shapes, sizes, densities, or diagnostic relevance. The combination of vertical adjustability, angular rotation, and stable support ensures that the imaging system 100 may achieve high spatial precision during data acquisition.

Figure 4:
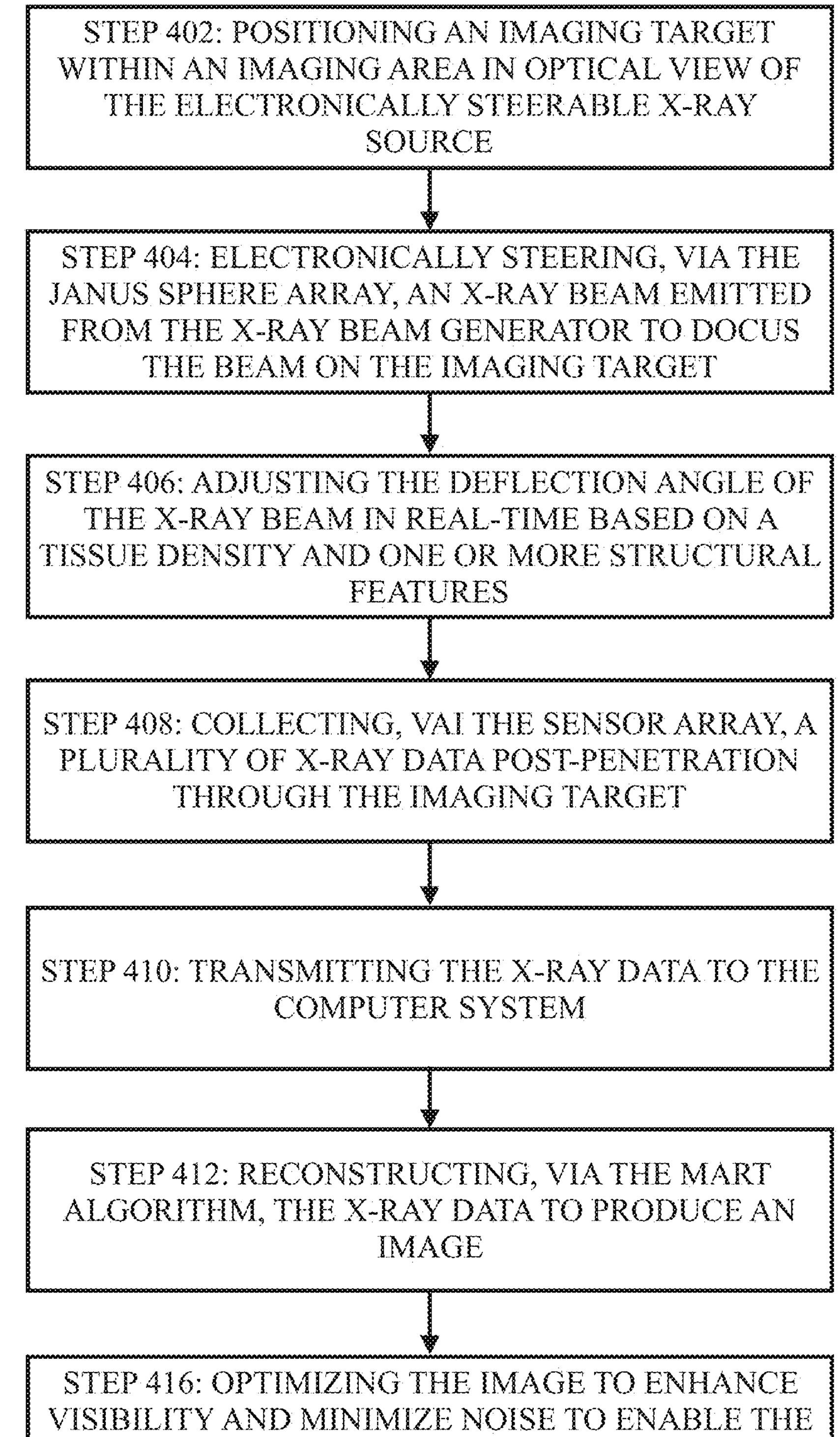
FIG. 4 is a flowchart illustrating a method for detecting a tumor in breast tissue using the electronically steerable x-ray imaging system, according to some embodiments.

FIG. 4 illustrates a flowchart representing a method 400 for detecting a tumor present in human breast tissue using an electronically steerable x-ray imaging system 100. The method may be implemented using the components described in connection with FIGS. 1 through 3B, including the electronically steerable x-ray source 110, x-ray beam generator 112, Janus sphere array 120, sensor array 140, and computer system 150.

At step 402, the method begins by positioning a breast within an imaging area in optical view of the electronically steerable x-ray source 110 and the sensor array 140. The imaging area may be defined by a patient platform 135 that aligns the imaging target 130 (e.g., the breast) with the vertical axis of the x-ray beam 114. The positioning may be performed manually by a technician or automatically using anatomical registration systems. Alignment guides, supports, or compression plates may be used to stabilize the breast and ensure consistent spatial orientation during the imaging process.

At step 404, the method includes electronically steering, via the Janus sphere array 120, an x-ray beam emitted from the x-ray beam generator 112 to focus the beam on the imaging target 130. The x-ray beam 114 may be directed through a dynamically adjustable Janus sphere array 120, which alters the deflection angle of the beam based on the refractive contrast between hemispheres of each Janus sphere 122. Steering may be controlled in real-time by a processor 152 of the computer system 150, which may execute instructions based on pre-scan configurations or anatomical models. The x-ray beam 114 may be focused on specific zones of interest, such as regions of high tissue density or previously marked areas.

At step 406, the deflection angle of the x-ray beam 114 is adjusted in real-time based on a tissue density and one or more structural features. Data from prior scans, scout images, or low-dose pre-imaging sequences may be analyzed to estimate local variations in breast tissue density. These estimates may be used to update the orientation of the Janus sphere array 120 or the position of the electronically steerable x-ray source 110 to optimize beam convergence. Structural features such as ducts, masses, or fibrous planes may also inform the beam trajectory. The beam steering adjustment may occur continuously or discretely at defined angular intervals.

At step 408, the method proceeds by collecting, via the sensor array 140, a plurality of x-ray data 116 post-penetration through the breast. The sensor array 140 may include linear or two-dimensional detector panels composed of x-ray sensitive materials such as amorphous silicon or CdTe. Each element in the sensor array 140 may register attenuation values corresponding to the x-ray photons that have passed through different regions of the breast tissue. The data may be captured at multiple angles, durations, or energy settings to maximize spatial resolution and contrast.

At step 410, the plurality of x-ray data 116 is transmitted to the computer system 150. The computer system 150 may include the processor 152, memory 154, and reconstruction software configured to operate a Multiplicative Algebraic Reconstruction Technique (MART) algorithm. The x-ray data 116 may be preprocessed to apply gain corrections, normalize detector responses, or interpolate missing values before being passed into the reconstruction pipeline. The data transfer may occur over high-speed wired or wireless channels, depending on the system configuration.

At step 412, the method includes reconstructing, via the MART algorithm, the plurality of x-ray data 116 to produce an image. The MART algorithm may iteratively update an image estimate based on the measured detector data and calculated projections, applying multiplicative corrections to individual voxel values. The processor 152 may compute forward projections, compare them with actual sensor data, and apply correction factors to enhance convergence, including inpainting. This reconstruction loop may repeat for a defined number of iterations or until a convergence threshold is met.

At step 414, the image is optimized to enhance visibility and minimize noise to enable detection of a tumor present in the breast. Optimization may include digital filtering, contrast enhancement, noise suppression, segmentation overlays highlighting regions with abnormal attenuation patterns or inpainting. These enhancements may be automatically generated or operator-adjustable via a user interface. The resulting image may be displayed on a diagnostic monitor 162 and stored in the system's data repository for further review, annotation, or comparison with prior scans.

The method 400 may be performed in whole or in part in real-time and may include optional subroutines such as adaptive scanning based on reconstruction feedback, or machine learning-based classification of suspicious features. FIG. 4 visually summarizes the method steps for transforming raw x-ray data into a high-resolution image capable of revealing tumors as small as 2-4 millimeters in diameter, as described elsewhere in this specification.

FIG. 5 illustrates a block diagram of the computer system 150 and associated software modules that collectively execute the steps of tumor detection, image reconstruction, and beam control as described in the method of FIG. 4. The system 150 may be implemented as a single-board embedded controller, a rack-mounted workstation, or a distributed server platform integrated into a clinical imaging suite. The architecture is designed to support high-speed data processing, adaptive control of the x-ray source, and iterative image reconstruction in real-time or near real-time. The system may be connected directly to the sensor array 140 and x-ray source 110 through high-speed data and control links. All modules shown in FIG. 5 may communicate via a system bus 160, which provides a common backbone for data movement between the processor 152, memory 154, storage 158, and external interfaces.

The processor 152 may include one or more central processing units (CPUs), graphics processing units (GPUs), tensor processing units (TPUs), or custom-designed processors such as FPGAs (Field-Programmable Gate Arrays) optimized for medical image reconstruction tasks.

In a typical configuration, the processor 152 supports parallel computing threads and SIMD (Single Instruction, Multiple Data) instructions, which are critical for performing the large matrix multiplications and iterative voxel updates involved in the MART algorithm. In GPU-accelerated variants, kernel operations may be offloaded to CUDA or OpenCL environments for increased throughput. The processor may also include onboard floating-point units (FPUs) and cache systems optimized for memory locality, which further accelerate convergence during iterative reconstruction. To support low-latency steering and feedback control, the processor 152 may operate under a real-time operating system (RTOS) or leverage priority threading mechanisms to handle hardware interrupts. This design would allow the computer system 150 to coordinate beam control and data processing with sub-millisecond precision.

The memory 154 is configured to store temporary and persistent data structures used throughout the reconstruction pipeline. This may include 3D voxel arrays representing attenuation coefficients, projection matrices for each scan angle, and intermediate outputs of the MART algorithm across iterations. The memory 154 may be segmented into dynamic memory buffers for incoming x-ray data 116, working copies of reconstruction matrices, and reserved regions for machine learning models or tissue templates. In systems with hardware acceleration, the memory 154 may also include dedicated shared memory blocks accessible to both the CPU and GPU. Memory paging and caching strategies may be employed to manage large datasets, such as volumetric breast scans exceeding several hundred megabytes. Synchronization between memory access threads ensures data integrity across iterations, especially during real-time updates to the image volume or convergence metrics.

The data interface 156 manages communication between the sensor array 140 and the reconstruction engine within the computer system 150. The interface may include analog-to-digital conversion modules, frame grabbers, or direct digital input ports capable of capturing high-fidelity signal streams from multi-element detector arrays. These interfaces may support data rates in the range of several gigabits per second to accommodate high-resolution, high-frame-rate scanning. Buffering mechanisms within the data interface 156 allow for smoothing of incoming data, preventing loss during processing delays or temporary memory saturation. Some embodiments may include adaptive error correction, time-stamp synchronization, and spatial calibration functions within the interface hardware itself. By preprocessing or structuring data at the interface level, the downstream pipeline benefits from reduced computational load and faster convergence. The data interface may also support backward communication to the sensor array for diagnostic, calibration, or gating commands.

The preprocessing module 510 conditions the x-ray data 116 before it enters the reconstruction stage. This module may normalize detector responses, apply dark-frame subtraction, and correct for spatial nonuniformities caused by geometric misalignment or sensor aging. In systems with dynamic beam steering, the preprocessing module may also align each projection frame to the correct beam orientation using encoder data from the x-ray source 110. Filtering operations such as median filters, Gaussian blurs, or wavelet denoising may be applied to reduce random noise in the raw projection data. In some implementations, statistical models of detector variance are used to estimate and compensate for measurement uncertainty on a per-pixel basis. The output of this module is typically a set of geometrically consistent, intensity-normalized projection datasets ready for reconstruction.

The reconstruction engine 520 orchestrates the MART algorithm, which is central to the system's ability to produce interpretable diagnostic images from projection data. The MART algorithm begins with an initial volume estimate, commonly a uniform attenuation grid or a blurred anatomical prior, and iteratively refines this estimate to minimize projection error. A forward projector 522 calculates simulated projections from the current image estimate using ray-tracing, Siddon's method, or algebraic projection algorithms. The correction module 524 then computes the difference between the simulated projections and the measured projections and generates multiplicative correction factors. These factors are applied voxel-by-voxel to the estimated image, modifying attenuation values based on local errors and convergence weights. A convergence monitor 526 evaluates the reconstruction progress by measuring projection consistency, entropy, or structural similarity index (SSIM), and terminates the iteration when a threshold is met or reconstruction quality plateaus.

Once reconstruction completes, the image volume is passed to the optimization module 530 for enhancement. This module improves tumor visibility and minimizes noise using spatial-domain or frequency-domain filters. For instance, Laplacian filters may be used to highlight edges, while bilateral filters preserve edges while reducing background grain. The optimization module may include dynamic range compression, histogram equalization, and region-growing segmentation to assist in clinical interpretation. Post-processing may also include confidence mapping, where heatmaps or color overlays indicate regions of higher diagnostic probability. In some cases, adaptive processing may be used to apply stronger denoising to regions of low interest and preserve full resolution in zones of suspected pathology.

The user interface module 540 provides the operator with direct control over system parameters and real-time access to reconstruction results. The interface may be rendered on a touchscreen display or controlled via keyboard and mouse. Users may adjust reconstruction parameters such as iteration count, convergence threshold, or voxel resolution. Interactive tools may include zoom, pan, measurement, annotation, and volumetric slicing. Real-time overlays may include beam steering paths, dose maps, or anatomical contours. The interface also provides alerts for system errors, out-of-range values, or scan completion, and may allow export to DICOM or other imaging standards.

A steering control module 550 interfaces with the electronically steerable x-ray source 110 and the Janus sphere array 120. This module converts real-time anatomical feedback, derived from the reconstruction engine 520 or machine learning classifiers, into updated steering instructions. The steering control module may adjust the position, angle, and intensity of the x-ray beam 114 by modifying servo positions, electromagnetic deflectors, or sphere array orientation. In some systems, the steering control module may synchronize with patient breathing cycles, cardiac rhythms, or automated robotic guidance systems for motion compensation. Parameters may be logged for reproducibility and radiation dosage auditing. The control logic may include safety overrides to prevent overexposure or ensure beam delivery remains within calibrated zones.

The storage device 158 may be implemented as a local solid-state drive, network-attached storage, or cloud-connected database. Data archived here may include raw projection data, reconstructed image volumes, session logs, beam steering paths, and user annotations. Metadata such as timestamp, patient ID, scan parameters, and image quality metrics may be embedded into each record. The system may compress datasets using lossless or diagnostically acceptable lossy algorithms to preserve storage space. Version-controlled storage of algorithm parameters and software updates ensures traceability and compliance in regulated environments. The storage device 158 may also maintain reference scans or training datasets used for algorithm calibration or validation.

In some configurations, FIG. 5 may include a machine learning integration module trained to assist with tumor detection and tissue classification. This module may operate downstream of the optimization module 530 or act as an advisor to the steering control module 550. Models may include convolutional neural networks (CNNs), support vector machines (SVMs), or transformer-based architectures trained on annotated medical image datasets. These models may output probability maps, segmentation masks, or diagnostic suggestions integrated into the clinician's workflow. Training data may include both simulated phantoms and retrospective clinical cases. Model explainability functions may be included to support regulatory review or user trust in the system's recommendations.

Altogether, the computer system 150 shown in FIG. 5 is a fully integrated, modular platform capable of transforming x-ray data 116 into high-resolution, optimized images. It performs a sequence of hardware and software operations that collectively enable tumor detection in human breast tissue while managing radiation dose, steering precision, and image clarity. The modularity of the system allows for flexible deployment in clinical, research, or mobile diagnostic environments. With support for real-time feedback, adaptive imaging, and machine-guided interpretation, the system is extensible to broader diagnostic applications beyond breast cancer detection. The architecture depicted in FIG. 5 thus supports both the technical and clinical requirements of next-generation medical imaging systems.

In some embodiments, the electronically steerable x-ray imaging system may incorporate beam modulation techniques in addition to beam steering. Electronic x-ray beam modulation refers to the ability to dynamically alter the x-ray beam's properties, such as shape, size, intensity distribution, energy, or pulse timing, through electrical or software control without requiring mechanical repositioning of the source or external collimators. This capability may be achieved by integrating electronically adjustable collimation mechanisms, aperture filters, or beam-shaping arrays directly into the x-ray beam generator 112. For example, a digitally controlled multi-leaf collimator or liquid crystal-based attenuation matrix may be used to mask or expose specific beam sectors during each exposure cycle. Alternatively, piezoelectric or electrostatic actuators may be used to move fine-scale shutters or modulate an embedded x-ray filter layer in response to control signals from the processor 152. By modifying beam parameters electronically, the system may achieve sub-second adaptation to patient anatomy, tissue density variations, or feedback from real-time image reconstruction.

The beam modulation feature may be integrated with the steering control module 550 to form a coordinated system capable of spatial and intensity targeting across the entire imaging area. For example, as the beam is electronically steered to a specific location within the imaging target 130, the modulation system may simultaneously reduce beam width or adjust beam intensity to match the attenuation characteristics of the targeted tissue region. This combined modulation and steering mechanism may improve tissue contrast and reduce artifacts caused by overexposure or under-illumination in heterogeneous anatomical structures. In addition, electronic modulation may allow for gradient dose distribution strategies, where central regions of interest receive higher beam intensities than surrounding tissues. Such strategies may be beneficial for reducing cumulative radiation exposure while preserving diagnostic accuracy in small lesion detection. Timing-based modulation may also be employed to synchronize short-duration beam pulses with moments of minimal tissue motion, such as during breath-hold cycles or cardiac quiet phases, as needed.

In certain configurations, the modulation system may include a beam-forming unit composed of an array of controllable elements, each corresponding to a sub-region of the emitted x-ray beam. These elements may operate independently or in coordinated patterns to shape the beam into rectangular, elliptical, or patient-specific projection profiles. Modulation instructions may be generated by the computer system 150 in response to live feedback from the sensor array 140 or based on a pre-scan planning image. The beam-forming unit may also enable techniques such as region-of-interest (ROI) imaging, where only a portion of the breast is exposed during high-resolution scanning, while peripheral areas receive minimal or no radiation. These advanced modulation patterns may be used in conjunction with the MART algorithm to enhance image fidelity in prioritized zones while conserving exposure in non-essential regions.

In some embodiments, the electronically steerable x-ray source 110 may be configured to generate variable-energy beams by modulating the voltage applied to the x-ray tube or switching between filter configurations. This energy modulation may be controlled on a per-frame or per-pulse basis to enable dual-energy or spectral imaging techniques. For example, the system may alternate between two energy levels during scan acquisition to capture energy-resolved attenuation profiles of the breast tissue, which may improve tissue classification or microcalcification detection, as in K-edge imaging. The modulation control system may maintain a synchronization table that links each energy state with the corresponding beam direction, sphere array deflection angle, and sensor array integration window. Data collected under different modulation conditions may be tagged with metadata and handled separately by the reconstruction engine 520 to preserve accuracy across multi-energy projections.

The integration of electronic x-ray beam modulation into the steerable imaging architecture provides an additional degree of control over the beam-tissue interaction, enabling imaging strategies that are adaptable, selective, and patient-specific. When combined with the MART reconstruction pipeline and real-time feedback, this capability allows the system to operate as an intelligent imaging platform capable of balancing diagnostic yield and radiation safety dynamically. The modulation features described herein may be implemented in hardware, firmware, or software, and may be configured or calibrated during system setup or scan protocol definition. These features may also be incorporated into regulatory logging, treatment planning interfaces, or dose-tracking subsystems to ensure transparency and repeatability in clinical workflows. By facilitating high-precision modulation of the x-ray beam, the system may support advanced breast imaging protocols and pave the way for integration with emerging AI-based targeting and adaptive radiomics techniques.

FIG. 6 illustrates a flowchart of a method performed by the processor 152 of the computer system 150 for reconstructing an image using a Multiplicative Algebraic Reconstruction Technique (MART) algorithm. The method depicted in FIG. 6 may be executed following the acquisition of a plurality of x-ray data 116 by the sensor array 140 after the electronically steerable x-ray beam 114 has passed through the imaging target 130. The steps shown in FIG. 6 represent an iterative computational process for generating a reconstructed image that corresponds to the internal structure of the breast and may be further processed to enhance tumor visibility and minimize image noise. As illustrated, the MART algorithm uses an initial image estimate and updates it through successive comparisons between simulated and measured projections, refining the voxel values in the image volume over multiple iterations. The reconstructed image produced by this method may then be used by downstream modules of the computer system 150 for optimization and tumor detection, as described in connection with FIGS. 4 and 5. Each step in the flowchart is labeled with a numerical identifier for clarity and traceability within the system architecture.

In step 600, the processor 152 of the computer system 150 receives a plurality of x-ray data 116 collected by the sensor array 140. The data corresponds to the attenuation of the electronically steered x-ray beam 114 after it has passed through the imaging target 130, such as human breast tissue. The sensor array 140 may include a matrix of digital detectors configured to capture high-resolution transmission data at multiple angular positions. Each detected data point represents the total x-ray energy received at a particular detector element and angle, and collectively, these values form a set of projection data. The data may be streamed directly into memory 154 or temporarily buffered via the data interface 156 for formatting and pre-processing. This projection data serves as the foundational input for initiating MART-based image reconstruction.

In step 605, the processor 152 initializes a voxel-based image estimate, which serves as the starting point for the iterative MART reconstruction. The image estimate may be represented as a three-dimensional matrix of attenuation coefficients that correspond spatially to the internal volume of the breast. Initialization may occur with a uniform constant value across all voxels, or with prior anatomical information derived from low-dose scout scans, previous patient studies, or population-based models. The resolution and size of the image estimate may be configured based on operator input or default protocol parameters. Initializing an accurate and well-scaled estimate can help reduce the number of required MART iterations and improve convergence stability. The image estimate is stored in memory 154 and updated dynamically during subsequent steps.

In step 610, the processor 152 computes a forward projection by simulating the passage of x-rays through the current image estimate along known beam trajectories. This is achieved using ray-tracing techniques or projection matrices based on the spatial relationship between the x-ray source 110, Janus sphere array 120, imaging target 130, and sensor array 140. The forward projector 522 calculates what the sensor array should have measured if the image estimate were fully accurate. The output of this operation is a simulated projection dataset with the same dimensional structure as the measured projection data received in step 600. This forward projection serves as a predictive baseline for evaluating the accuracy of the current image estimate. Any discrepancies between simulated and measured projections indicate areas where the image estimate must be corrected.

In step 615, the system performs an element-wise comparison between the simulated projections from step 610 and the actual measured projection data from step 600. This comparison identifies regions where the current image estimate overestimates or underestimates the true x-ray attenuation along specific beam paths. Differences may be calculated as ratios, logarithmic errors, or other quantitative discrepancies suitable for use in multiplicative correction. These error values may be stored in a temporary buffer and indexed according to their corresponding beam paths and detector elements. The comparison may also generate error maps or residual plots, which can be used to monitor convergence progress over time. Identifying and quantifying these differences is essential for determining how the image estimate should be updated.

In step 620, the processor 152 computes correction factors for each voxel in the image estimate based on the projection errors identified in step 615. For each voxel intersected by a given x-ray beam path, the system determines how much that voxel contributed to the simulated error and assigns a multiplicative correction accordingly. This correction factor may be the ratio of the measured value to the simulated value, weighted by the voxel's path length and normalized to prevent overcorrection. Corrections from multiple beam paths may be aggregated and applied iteratively or averaged to achieve a balanced update. The correction process ensures that the most inconsistent regions of the image estimate are adjusted more aggressively, while stable regions receive minimal changes. This approach allows MART to converge efficiently while preserving structural fidelity.

In step 625, the processor 152 applies the multiplicative correction factors computed in step 620 to the current image estimate stored in memory 154. Each voxel value in the image matrix is updated by multiplying it by its corresponding correction factor, effectively increasing or decreasing attenuation values based on local error. The update is performed voxel-wise and may be constrained by boundary conditions, regularization terms, or prior anatomical constraints to avoid non-physical values. After all voxels have been updated, the revised image estimate becomes the new basis for the next forward projection. The update may be performed in-place or written to a separate memory block for version tracking. This step is repeated iteratively to drive the image estimate closer to alignment with the measured data.

In step 630, the system evaluates whether a convergence condition has been satisfied, indicating that further updates may no longer improve the image estimate meaningfully. Convergence may be assessed by calculating the average or maximum residual between measured and simulated projections, monitoring changes in voxel values between iterations, or evaluating image quality metrics such as entropy or contrast. A user-defined threshold or algorithmically determined stopping condition may be used to terminate the reconstruction loop. If convergence is detected, the reconstruction process proceeds to the final output step. If not, the system returns to step 610 to begin the next iteration using the newly updated image estimate, unless total dose is unacceptable. This step ensures computational efficiency and prevents unnecessary over-processing of the image volume.

In step 635, the system re-enters the iterative loop if the convergence criteria from step 630 have not yet been satisfied. The processor 152 repeats the sequence of forward projection, error comparison, correction computation, and image update as described in steps 610 through 625. With each iteration, the image estimate is refined and brought into closer alignment with the actual projection data collected from the sensor array 140. The number of iterations may vary depending on the complexity of the anatomy, the noise characteristics of the data, and the initial estimate used. Some embodiments may cap the total number of iterations or implement dynamic iteration scaling based on reconstruction quality trends. This loop continues until convergence is achieved or a termination condition is met.

In step 640, once the image estimate has converged, the final reconstructed image is output by the processor 152 and passed to downstream modules for visualization and analysis. The reconstructed image may be a 2D slice, a volumetric 3D dataset, or a series of projection images, depending on the scan configuration and reconstruction geometry. The output image is written to the memory 154 and may be displayed to the operator via the user interface 540 or stored in the storage device 158. At this stage, the image preserves anatomical detail and localized attenuation features required for clinical interpretation. The output may also include metadata such as beam angles, exposure settings, and iteration counts for audit and traceability purposes. This image serves as the input for subsequent enhancement and tumor detection workflows. One possibility is automatic ablation of any 2-4 mm tumors using a focusing polycapillary x-ray source.

In step 645, the image undergoes post-reconstruction optimization to enhance diagnostic utility, particularly for tumor detection. The processor 152 may apply contrast enhancement algorithms, spatial filters, noise suppression techniques, and segmentation overlays to highlight anatomical features of interest. Optimization may include adaptive sharpening, background equalization, and suppression of reconstruction artifacts that could obscure small or low-contrast lesions. These operations improve tumor visibility by increasing the signal-to-noise ratio (SNR) and contrast-to-noise ratio (CNR) in relevant regions of the image. The resulting optimized image may be further processed by tumor detection algorithms or reviewed manually by a clinician. By combining MART-based reconstruction with intelligent post-processing, the system ensures that the final image is both high in fidelity and diagnostically actionable.

In certain embodiments, the electronically steerable x-ray imaging system 100 may implement adaptive beam control to dynamically adjust one or more beam parameters in response to anatomical variations or imaging data acquired during a scan. Adaptive beam control may include automatic or semi-automatic modifications to the beam's direction, focus, intensity, shape, or dwell time based on real-time analysis of tissue structure, density gradients, or signal quality. The processor 152 may continuously evaluate data from the sensor array 140, including attenuation profiles or noise levels, and issue updated control instructions to the x-ray beam generator 112, Janus sphere array 120, or any electronically modulated beam-shaping components. In systems equipped with a feedback-enabled steering control module 550, the adaptive control loop may operate at sub-second intervals, allowing the beam to "follow" regions of interest or re-target under-sampled tissue zones during a single scan session. This level of closed-loop responsiveness may be achieved through software integration between the reconstruction engine 520 and the steering subsystem, using error metrics, convergence profiles, or spatial entropy maps as real-time guidance inputs.

The adaptive beam control system may be configured to optimize imaging performance by modifying exposure and beam trajectory according to local tissue characteristics. For example, denser or more radiopaque areas of the breast, such as glandular regions or suspected lesions, may trigger increased beam intensity, narrower focus, or finer steering resolution to improve image clarity. Conversely, regions with low clinical relevance or homogeneous composition may be imaged with broader beams or fewer angular samples to conserve radiation dose and reduce acquisition time. These adaptations may be performed using rule-based protocols, operator-defined regions of interest, or intelligent algorithms trained on clinical imaging datasets. The adaptive control framework may also accommodate anatomical diversity across patient populations, adjusting for differences in breast size, tissue composition, or prior surgical modifications. These features enable patient-specific scan tailoring without requiring hardware repositioning or operator intervention between scan phases.

In some implementations, the adaptive beam control system may utilize information from preliminary scans, reference models, or prior imaging sessions to guide initial steering trajectories and parameter presets. For example, if a patient previously underwent imaging that identified a lesion in a specific quadrant of the breast, the system may prioritize beam resolution and intensity in that region during future scans. Alternatively, the system may begin with a low-dose scout scan and analyze that data in real time to determine the optimal scan sequence, including angular coverage, exposure levels, and projection density. This predictive adaptation process may also incorporate tissue segmentation maps, anatomical atlases, or population-based priors to inform steering logic. These adaptations can be executed without interrupting the primary imaging workflow, allowing seamless transitions between low-resolution survey imaging and high-resolution diagnostic targeting within a single protocol.

The adaptive beam control system may also interface with user-defined scan presets or manual override options. A technician may define zones of diagnostic interest within the graphical user interface 540, assigning imaging priorities or constraints such as maximum dose, minimum resolution, or scan time limits. The adaptive control module may use this input to shape beam control logic, balancing real-time optimization with user intent and system constraints. In advanced deployments, the user interface may visualize adaptive beam paths, exposure gradients, and anticipated imaging outcomes before execution, enabling informed decisions and greater transparency. Logging of adaptive adjustments, including beam angles, intensities, and control decisions, may be stored in the storage device 158 for audit, review, or regulatory reporting.

When integrated with electronic x-ray beam modulation features, adaptive beam control provides a dual-layer adjustment capability, enabling both geometric and parametric optimization of the imaging beam. This combination allows the system to focus on high-yield diagnostic regions while avoiding unnecessary exposure to surrounding tissues, a feature particularly useful in breast imaging where dense tissue regions may obscure small lesions. The system may automatically tune exposure durations, beam shaping profiles, and angular sampling density to match the signal-to-noise characteristics of each region scanned. In certain configurations, adaptive control may be implemented as a plug-in or software layer, making it deployable across multiple imaging hardware platforms with minimal changes to core electronics. The adaptive beam control architecture thus provides a pathway for intelligent, patient-specific imaging that enhances diagnostic performance while supporting safe and efficient operation.

The electronically steerable x-ray imaging system 100 may also incorporate scattering reduction steering, a feature configured to minimize the impact of scattered radiation on image quality during breast imaging procedures. Scattered radiation typically arises when x-ray photons interact with tissue at oblique angles or heterogeneous interfaces, resulting in off-angle photons reaching the detector and contributing to image noise. In the disclosed system, scattering reduction steering may be achieved by electronically manipulating the direction of the x-ray beam 114 and adjusting the beam's incidence angle on the imaging target 130. The processor 152, in communication with the steering control module 550, may coordinate the angle and trajectory of the x-ray beam emitted from the x-ray beam generator 112 to limit beam entry paths that are known to generate excessive scatter, particularly in peripheral or dense tissue zones. These paths may be pre-mapped through simulation or adaptively determined during preliminary scan phases. In some implementations, the Janus sphere array 120 may also be dynamically adjusted to fine-tune beam deflection and concentrate radiation along optimal transmission vectors with minimal angular dispersion.

To support scattering reduction, the system may optimize the geometry between the x-ray source 110, the Janus sphere array 120, the imaging target 130, and the sensor array 140. Beam steering may be constrained to preferred angular windows known to produce lower scatter intensities based on empirical tissue models or attenuation profiles. For example, shallow-angle entries into high-density glandular tissue may be minimized, while more orthogonal beam paths may be favored to enhance transmission and reduce off-axis scattering. The steering algorithm may adjust not only the angle of incidence but also the lateral translation and focus of the beam to avoid border zones and edge artifacts, which often serve as scatter sources. In certain embodiments, the beam may be steered away from previously imaged or high-scatter zones and focused on under-sampled areas to maintain image uniformity and reduce cumulative scatter buildup across frames. This approach allows the system to limit the contribution of low-energy, scattered photons that degrade contrast and obscure fine details such as microcalcifications. Alternatively, more complex algorithms can incorporate scattered x-rays as data.

In conjunction with geometric steering, scattering reduction may also involve selective gating or modulation of the beam to limit exposure to scatter-prone anatomical regions. For instance, during a multi-angle scan sequence, the system may selectively suppress beam output at steering positions where the projected scatter-to-primary ratio (SPR) exceeds a defined threshold. These decisions may be informed by Monte Carlo simulations, beam path databases, or real-time feedback from the sensor array 140. If the sensor array includes dedicated anti-scatter detection rows or signal isolation circuitry, the system may actively measure scatter components and use this data to influence subsequent beam steering paths. Additionally, directional filtering or post-processing scatter correction algorithms may be applied to projection data from angles with unavoidable scatter contributions. These strategies work synergistically with steering logic to enhance contrast and reduce false positive detections caused by photon noise or overlapping anatomical features.

The Janus sphere array 120 may be particularly useful for steering beams in a manner that inherently limits scatter by controlling divergence and beam width. Each Janus sphere 122 may be oriented to selectively bend rays toward the central portion of the imaging target 130, thereby minimizing peripheral illumination where scatter is more pronounced. In some configurations, the Janus spheres may be dynamically repositioned or replaced by programmable metamaterial lenses or gratings to enhance beam collimation. The steering geometry may also be paired with beam hardening filters or aperture masks to shape the spectrum and angular spread of the beam in scatter-sensitive regions. Real-time optimization routines running on the processor 152 may compare measured scatter signal profiles against predicted models and adjust the beam direction or energy accordingly. This feedback-enabled design allows the system to iteratively reduce scatter effects throughout the course of a scan session, thereby improving image uniformity and diagnostic clarity.

Scattering reduction steering provides particular benefits in breast imaging, where tissue heterogeneity, high contrast interfaces, and curved anatomy often result in elevated scatter levels. By intelligently steering and modulating the beam, the system may preserve detail in critical diagnostic areas, such as near the chest wall or in regions with prior surgical intervention. When combined with the MART algorithm and adaptive reconstruction weighting, steering-based scatter reduction may also improve convergence and suppress noise propagation in the reconstructed image. The ability to reduce scatter electronically, without reliance on physical anti-scatter grids, may further simplify system design, reduce cost, and enhance compatibility with low-dose imaging protocols. In sum, the steering mechanisms described herein may be configured to selectively direct x-ray energy along paths that inherently reduce scatter generation, enhance transmission signal fidelity, and improve overall image quality in the detection of breast tumors.

The electronically steerable x-ray imaging system 100 may be configured to detect a tumor present in human breast tissue by analyzing a reconstructed image generated from a plurality of x-ray data 116. The process of tumor detection begins with the emission and electronic steering of an x-ray beam 114 from the x-ray beam generator 112 through the Janus sphere array 120 and into the imaging target 130. After the beam penetrates the tissue, the sensor array 140 collects attenuation data from multiple angles or scan passes, producing a multidimensional dataset that reflects spatial variations in tissue density. These variations may include localized increases in attenuation caused by tumors, lesions, or dense fibroglandular regions. The collected x-ray data 116 is transmitted to the computer system 150, where the processor 152 applies the MART algorithm to reconstruct a high-resolution image volume. The reconstructed image preserves voxel-level intensity gradients, allowing detailed analysis of structural abnormalities with sub-millimeter spatial resolution.

The system may detect tumors by identifying regions within the reconstructed image that exhibit attenuation patterns characteristic of neoplastic tissue. Tumors may present as discrete regions of elevated x-ray attenuation compared to surrounding fatty or glandular tissue, often with irregular or lobulated borders. The image optimization module 530 may enhance these features by applying contrast enhancement, edge detection, and localized filtering to highlight suspicious zones. In some embodiments, the processor 152 may automatically segment the reconstructed image and compare voxel clusters against stored attenuation templates or histological profiles to identify features consistent with tumor morphology. The user interface 540 may display these regions with visual overlays, bounding boxes, or false-color maps to assist radiologists in diagnosis. The system may also allow the user to select a suspected tumor region for further scanning, prompting the steering control module 550 to re-target the beam for increased angular sampling or enhanced resolution.

Detection sensitivity may be further improved through the use of adaptive reconstruction algorithms that prioritize convergence in regions with high anatomical complexity. The MART algorithm may weight iterative updates more heavily in areas with steep attenuation gradients, which often coincide with tumor boundaries. This localized weighting allows for improved contrast around subtle or early-stage tumors that might otherwise be lost in noise or partial volume effects. Additionally, the system may detect tumors as small as 2 to 4 millimeters in diameter, depending on beam geometry, detector resolution, and scan configuration. The ability to resolve tumors at this scale supports early detection strategies and may reduce the need for confirmatory imaging or invasive biopsies. All tumor detection processes may be documented in a scan session log, including spatial coordinates, attenuation values, and classification scores for future comparison or treatment planning.

In certain implementations, the tumor detection capability may be enhanced through machine learning models trained on labeled imaging datasets. These models may operate downstream of the reconstruction engine 520, taking as input the optimized image volume and outputting segmentation masks, probability scores, or classification labels. The system may employ convolutional neural networks (CNNs), U-Net architectures, or decision-tree ensembles to identify and delineate tumors with high specificity. These AI-based detection features may be used as secondary readers or decision-support tools, offering additional diagnostic confidence to radiologists. Detected tumors may be cross-referenced with prior imaging studies stored in the storage device 158 to assess progression or treatment response. The system may also record metadata associated with each detection event, including detection time, model version, and confidence score, to ensure traceability and clinical accountability.

When integrated with adaptive beam control and scattering reduction steering, the tumor detection process becomes a closed-loop system wherein the image reconstruction, analysis, and beam delivery are continually refined to improve detection accuracy. For example, if a suspected tumor is identified during preliminary scan phases, the steering control module 550 may adjust the beam path to collect additional projections at that location, enhancing tumor reconstruction fidelity. The MART algorithm may incorporate prior knowledge of the tumor's location into its initialization or update weighting, focusing computational resources on the region of interest. As more data is acquired, the detection confidence may increase, and the system may prompt the operator to annotate or mark the tumor site within the user interface 540. This dynamic, data-driven approach ensures that suspected tumors receive the necessary imaging attention while maintaining efficiency and minimizing unnecessary exposure elsewhere in the breast. Through these combined features, the system may support accurate, early-stage tumor detection and improve diagnostic workflows in breast cancer screening and follow-up imaging.

The electronically steerable x-ray imaging system described herein constitutes a technological improvement to a physical imaging apparatus, rather than an abstract idea or mathematical operation performed in isolation. The claimed subject matter is rooted in the practical field of medical imaging, where an electronically steerable x-ray source cooperates with a Janus sphere array, a sensor array, and a processor-controlled reconstruction engine to produce tangible diagnostic images. Each step performed by the computer system is tied to the physical acquisition, transformation, and interpretation of x-ray energy interacting with biological tissue. The system's computing operations directly modify the physical control of the x-ray beam in real time, resulting in a measurable change in radiation output, beam direction, and tissue exposure profile. Accordingly, the claimed processes are not abstract data manipulations but are technologically grounded implementations that transform physical x-ray data into diagnostically actionable images through concrete machine operations.

The processor of the computer system executes the MART algorithm as part of a specialized imaging architecture, not as a generic computer function. The MART algorithm is implemented in connection with calibrated detector geometry, controlled beam steering, and voxel-based image modeling that are specifically adapted to x-ray physics. The algorithm requires iterative comparison of measured and simulated x-ray projections generated by the physical imaging system, thereby integrating real-world data acquisition and machine-controlled feedback. The hardware configuration, including the electronically steerable source, sensor array, and Janus sphere array, cannot perform its intended function without the coordinated computing process. This interdependence demonstrates that the claimed computer operations produce a practical technical effect, distinguishing the subject matter from disembodied mathematical concepts or abstract diagnostic reasoning.

The claimed computer system also provides a specific technical improvement to computer functionality itself, as it executes an adaptive reconstruction workflow that dynamically adjusts processing parameters based on feedback from the sensor array. Unlike conventional processors that merely perform fixed image reconstruction steps, the system disclosed herein continuously modulates its computational weighting and steering commands to achieve convergence in fewer iterations. This adaptive loop enhances computational efficiency, reduces noise propagation, and improves image clarity while minimizing patient radiation exposure. The processor's interaction with the electronically steerable source represents a non-conventional and non-routine integration of computing and imaging technologies.

Furthermore, the claimed subject matter provides a tangible transformation of data and matter. The x-ray data received from the sensor array represents physical energy attenuated through the imaging target; this energy is then converted into electrical signals, processed by the computer system, and output as a reconstructed image displayed on a physical monitor. The computing system thus performs a series of transformations, radiation to electrical signals, signals to digital data, and digital data to a visual image, that yield a useful and concrete result in the field of diagnostic imaging. Because these operations are inherently physical, the claims are directed to patent-eligible processes and machines, not to abstract principles.

Many different embodiments have been disclosed herein, in connection with the above description and the drawings. It will be understood that it would be unduly repetitious and obfuscating to literally describe and illustrate every combination and subcombination of these embodiments. Accordingly, all embodiments can be combined in any way and/or combination, and the present specification, including the drawings, shall be construed to constitute a complete written description of all combinations and subcombinations of the embodiments described herein, and of the manner and process of making and using them, and shall support claims to any such combination or subcombination.

The foregoing is provided for purposes of illustrating, explaining, and describing embodiments of this disclosure. Modifications and adaptations to these embodiments will be apparent to those skilled in the art and may be made without departing from the scope or spirit of this disclosure.

As used herein and in the appended claims, the singular forms "a", "an", and "the" include plural referents unless the context clearly dictates otherwise.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

In many instances entities are described herein as being coupled to other entities. It should be understood that the terms "coupled" and "connected" (or any of their forms) are used interchangeably herein and, in both cases, are generic to the direct coupling of two entities (without any non-negligible (e.g., parasitic intervening entities) and the indirect coupling of two entities (with one or more non-negligible intervening entities). Where entities are shown as being directly coupled together or described as coupled together without description of any intervening entity, it should be understood that those entities can be indirectly coupled together as well unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

An equivalent substitution of two or more elements can be made for any one of the elements in the claims below or that a single element can be substituted for two or more elements in a claim. Although elements can be described above as acting in certain combinations and even initially claimed as such, it is to be expressly understood that one or more elements from a claimed combination can in some cases be excised from the combination and that the claimed combination can be directed to a subcombination or variation of a subcombination.

It will be appreciated by persons skilled in the art that the present embodiment is not limited to what has been particularly shown and described herein. A variety of modifications and variations are possible in light of the above teachings without departing from the following claims.

What is claimed is:

1. An electronically steerable x-ray imaging system, comprising:

an electronically steerable x-ray source including an x-ray beam generator to emit an x-ray beam;

a sphere array to enable electronic steering of the x-ray beam;

an imaging target comprising human breast tissue to receive the x-ray beam;

a sensor array positioned to detect the imaging target and to detect a plurality of x-ray data post-penetration through the human breast tissue;

a computer system including a processor configured to perform the following:

receive the plurality of x-ray data from the sensor array;

reconstruct an image from the plurality of x-ray data using a Multiplicative Algebraic Reconstruction Technique (MART) algorithm, wherein the MART algorithm iteratively compares measured projections with simulated projections to generate one or more reconstruction quality metrics;

optimize tumor visibility and minimize noise contained in the image; and adjust, in real-time and in a closed-loop feedback manner, one or more steering parameters of the electronically steerable x-ray source and one or more imaging parameters based on the one or more reconstruction quality metrics and on a tissue density and a structural feature identified from the plurality of x-ray data, such that intermediate reconstruction outputs from the MART algorithm update the one or more steering parameters to refine image fidelity during an ongoing scan.

2. The electronically steerable x-ray imaging system of claim 1, wherein the x-ray beam generator emits the x-ray beam within an energy range between 30-50 keV.

3. The electronically steerable x-ray imaging system of claim 1, wherein steering the x-ray beam enables control over a direction and an intensity delivered to the imaging target.

4. The electronically steerable x-ray imaging system of claim 1, wherein the sphere array deflects the x-ray beam at a pre-determined angle to optimize focus of the x-ray beam on the imaging target.

5. The electronically steerable x-ray imaging system of claim 1, wherein the imaging target is a breast phantom utilized during a simulation or attesting procedure, wherein the breast phantom replicates the human breast tissue.

6. The electronically steerable x-ray imaging system of claim 1, wherein the computer system is further configured to execute the MART algorithm to iteratively update voxel values by computing multiplicative correction factors derived from a ratio between the measured projections and the simulated projections, and to process the x-ray data to reconstruct a plurality of high-resolution images.

7. The electronically steerable x-ray imaging system of claim 1, wherein the electronically steerable x-ray source is capable of adjusting a direction, an intensity, and a focus of the x-ray beam in real-time.

8. The electronically steerable x-ray imaging system of claim 1, wherein the sphere array is constructed of a plurality of Janus spheres to control a deflection angle of the x-ray beam, wherein each Janus sphere of the plurality of Janus spheres comprises two hemispherical regions formed from distinct materials having different x-ray refractive indices, and wherein the plurality of Janus spheres is arranged in a lattice mounted in a substrate or flexible membrane that permits positional adjustment of the plurality of Janus spheres by a motorized stage, an electrostatic field generator, or a magnetic actuator to modify, in real-time, the deflection angle in response to feedback from the sensor array.

9. The electronically steerable x-ray imaging system of claim 1, wherein the one or more of the steering parameters comprise at least one of angular deflection of the x-ray beam, exposure duration, pulse repetition frequency, and spatial scanning trajectory, and wherein the one or more imaging parameters comprise at least one of voxel size, sampling resolution, and reconstruction filter weights.

10. An electronically steerable x-ray imaging system, comprising:

an electronically steerable x-ray source including an x-ray beam generator to emit an x-ray beam;

a Janus sphere array to enable electronic steering of the x-ray beam by adjusting a deflection angle of the x-ray beam, wherein the Janus sphere array comprises a plurality of Janus spheres each comprising two hemispherical regions formed from distinct materials having different x-ray refractive indices;

an imaging target comprising human breast tissue to receive the x-ray beam;

a sensor array positioned to detect the imaging target and to detect a plurality of x-ray data post-penetration through the human breast tissue;

a computer system including a processor configured to perform the following:

receive the plurality of x-ray data from the sensor array;

reconstruct an image from the plurality of x-ray data using a Multiplicative Algebraic Reconstruction Technique (MART) algorithm, wherein the MART algorithm iteratively refines the image by computing a forward projection from a current image estimate, comparing the forward projection with the plurality of x-ray data to identify projection errors, and applying multiplicative correction factors to voxel values of the current image estimate based on the projection errors;

optimize tumor visibility and minimize noise contained in the image, wherein the sensor array is capable of detecting a tumor between about 2-4 mm within the human breast tissue; and adjust, in real-time and in a closed-loop feedback manner during an ongoing scan, the deflection angle of the Janus sphere array and one or more steering parameters of the electronically steerable x-ray source based on (i) intermediate reconstruction outputs of the MART algorithm and (ii) a tissue density and one or more structural features identified from the plurality of x-ray data.

11. The electronically steerable x-ray imaging system of claim 10, wherein the x-ray beam generator emits the x-ray beam within an energy range between 30-50 keV.

12. The electronically steerable x-ray imaging system of claim 11, wherein steering the x-ray beam enables control over a direction and an intensity delivered to the imaging target.

13. The electronically steerable x-ray imaging system of claim 12, wherein the sphere array deflects the x-ray beam at a pre-determined angle to optimize focus of the x-ray beam on the imaging target.

14. The electronically steerable x-ray imaging system of claim 13, wherein the imaging target is a breast phantom utilized during a simulation or attesting procedure, wherein the breast phantom replicates the human breast tissue.

15. The electronically steerable x-ray imaging system of claim 14, wherein the computing system operates a Multiplicative Algebraic Reconstruction Technique (MART) algorithm to process the x-ray data to reconstruct a plurality of high-resolution images.

16. The electronically steerable x-ray imaging system of claim 15, wherein the electronically steerable x-ray source is capable of adjusting a direction, an intensity, and a focus of the x-ray beam in real-time.

17. The electronically steerable x-ray imaging system of claim 16, wherein the computer system is capable of adjusting one or more steering parameters and one or more imaging parameters based on a tissue density and a structure.

18. A method for detecting a tumor present in human breast tissue using an electronically steerable x-ray imaging system, the method comprising the steps of:

positioning a breast within an imaging area in optical view of an electronically steerable x-ray source and a sensor array;

electronically steering, via a Janus sphere array, an x-ray beam emitted from an x-ray beam generator to focus the x-ray beam on an imaging target;

adjusting a deflection angle of the x-ray beam in real-time based on a tissue density and one or more structural features;

collecting, via the sensor array, a plurality of x-ray data post-penetration through the breast;

transmitting the plurality of x-ray data to a computer system, the computer system operating a processor configured to perform the following steps:

reconstructing, via a Multiplicative Algebraic Reconstruction Technique (MART) algorithm, the plurality of x-ray data to produce an image, wherein the MART algorithm iteratively updates voxel values of the image by (i) computing a forward projection from a current image estimate, (ii) comparing the forward projection against the plurality of x-ray data to identify projection errors, and (iii) applying multiplicative correction factors derived from the projection errors to the voxel values;

evaluating one or more reconstruction quality metrics generated by the MART algorithm during the reconstructing;

dynamically updating, in a closed-loop feedback manner during the reconstructing, the deflection angle of the Janus sphere array and one or more steering parameters of the electronically steerable x-ray source based on the one or more reconstruction quality metrics, such that intermediate reconstruction outputs of the MART algorithm refine image fidelity during an ongoing scan; and optimizing the image to enhance visibility and to minimize noise contained in the image to enable detection of a tumor present in the breast, wherein the tumor is between about 2 and 4 millimeters in diameter.

19. The method of claim 18, wherein steering the x-ray beam enables control over a direction and an intensity delivered to the imaging target.

20. The method of claim 19, wherein the sphere array deflects the x-ray beam at a pre-determined angle to optimize focus of the x-ray beam on the imaging target.

* * * * *